(12) United States Patent
Halloran et al.

(10) Patent No.: US 8,841,486 B2
(45) Date of Patent: Sep. 23, 2014

(54) STEREOSELECTIVE SYNTHESIS OF METYROSINE

(75) Inventors: Kevin John Halloran, Somerset, NJ (US); Alex Comely, Barcelona (ES); Zhengming Chen, Belle Mead, NJ (US); Shyam Krishnan, San Francisco, CA (US)

(73) Assignee: Aton Pharma, Bridgewater, NJ (US)

( * ) Notice: Subject to any disclaimer, the term of this patent is extended or adjusted under 35 U.S.C. 154(b) by 174 days.

(21) Appl. No.: 12/916,318

(22) Filed: Oct. 29, 2010

(65) Prior Publication Data
US 2011/0104765 A1    May 5, 2011

Related U.S. Application Data

(60) Provisional application No. 61/256,926, filed on Oct. 30, 2009.

(51) Int. Cl.
*C07C 221/00* (2006.01)
*C07C 223/00* (2006.01)
*C07C 225/00* (2006.01)
*C07C 255/43* (2006.01)
*C07C 231/06* (2006.01)
*C07C 227/20* (2006.01)
*C07C 237/20* (2006.01)
*C07C 231/24* (2006.01)
*C07C 253/00* (2006.01)
*C07C 231/12* (2006.01)
*C07C 249/02* (2006.01)
*C07C 251/24* (2006.01)
*C07C 227/32* (2006.01)
*C07C 229/36* (2006.01)
*C07C 231/18* (2006.01)

(52) U.S. Cl.
CPC .............. *C07C 253/00* (2013.01); *C07C 255/43* (2013.01); *C07C 231/06* (2013.01); *C07C 227/20* (2013.01); *C07C 237/20* (2013.01); *C07C 231/24* (2013.01); *C07C 231/12* (2013.01); *C07C 249/02* (2013.01); *C07C 251/24* (2013.01); *C07C 227/32* (2013.01); *C07C 229/36* (2013.01); *C07B 2200/07* (2013.01); *C07C 231/18* (2013.01)
USPC ........................................................ 564/344

(58) Field of Classification Search
None
See application file for complete search history.

(56) References Cited

U.S. PATENT DOCUMENTS

| 6,096,745 A | 8/2000 | Poindexter et al. |
| 6,528,686 B1 | 3/2003 | Akamatsu et al. |
| 6,610,731 B2 | 8/2003 | Duan et al. |
| 6,949,658 B2 | 9/2005 | Katoh et al. |

FOREIGN PATENT DOCUMENTS

| JP | 63255255 | * 10/1988 | ............ C07C 101/30 |
| WO | WO-2011/053835 A1 | 5/2011 | |

OTHER PUBLICATIONS

Boesten et al. Org Lett. 2001, vol. 3, No. 8, pp. 1121-1124.*
Weinges et al. Chemische Berichte (1977), 110 (6), 2098-2105.*
Weinges et al. Chemische Berichte (1977), 110 (6), 2098-2105 (Derwent Abstract).*
JP63255255 Derwent ABS 1988 pp. 1-5.*
International Search Report for PCT/US2010/054814 mailed Jan. 14, 2011.
Wuts et al., Greene's Protective Groups in Organic Synthesis, 4th Edition, 2006. [T.O.C.].
Björkling et al., "Enzyme catalysed hydrolysis of dialkylated propanedioic acid diesters, synthesis of optically pure (S)-alpha-methylphenylalanine, (S)-alpha-methyltyrosine and (S)-alpha-methyl-3,4-dihydroxyphenylalanine," Tetrahedron Letters 26(40): 4957-4958 (1985).
Potts, "Some alpha-Methylamino-acids," J. Chem. Soc. 1632-1634 (1955).
Saari, "Reaction of nitro anions with N,N-dimethyl-p-hydroxybenzylamine: a new synthesis of alpha-methyltyrosine," J. Org. Chem. 32, pp. 4074-4076 (1967).
Stein et al, "Alpha-methyl alpha-amino acids. II. Derivatives of DL-phenylalanine," J. Am. Chem. Soc. 77: 700-703 (1955).
Vardanyan et al., "Synthesis of essential drugs," 2006 edition, p. 177.
Weinges et al., "Asymmetric synthesis. II. External asymmetric Strecker synthesis of alpha-methylamino acids," Chem. Ber. 104(11):3594-3606 (1971).

* cited by examiner

*Primary Examiner* — Clinton Brooks
(74) *Attorney, Agent, or Firm* — Toan P. Vo; Timothy J. Shea, Jr.; Matthew S. Bodenstein

(57) ABSTRACT

Provided herein are compositions including diastereomers in substantially diastereomerically pure form and enantiomers in substantially enantiomerically pure form, and processes for preparing them and converting them to metyrosine.

8 Claims, No Drawings

STEREOSELECTIVE SYNTHESIS OF METYROSINE

CROSS-REFERENCE TO RELATED PATENT APPLICATIONS

This application claims priority from U.S. Provisional Application 61/256,926, filed Oct. 30, 2009, incorporated herein by reference in its entirety.

FIELD

The present technology relates to compositions and processes useful for the stereoselective synthesis of metyrosine and relates generally to the field of organic chemistry.

BACKGROUND

Metyrosine, which has the structure of Formula:

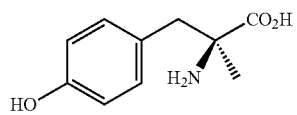

is useful in reducing elevated levels of catecholamines associated with pheochromocytoma, and preventing hypertension. Metyrosine, as shown, is a chiral compound. The synthesis of metyrosine in pure or substantially pure enantiomeric form requires a process that involves using substantially diastereomerically and/or enantiomerically pure intermediates. The Applicant has discovered, surprisingly, certain compounds that are substantially diastereomerically or enantiomerically pure and processes to prepare them, and which compounds may be converted to metyrosine.

SUMMARY

Compositions are provided that include diastereomers in substantially diastereomerically pure form and enantiomers in substantially enantiomerically pure form. Processes are provided for preparing the diastereomers and enantiomers. Processes for converting the diastereomers and enantiomers to metyrosine are also provided.

In one aspect, a process is provided for the synthesis of a compound of Formula II:

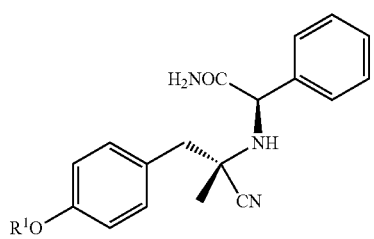

including contacting in a solution a compound of Formula I:

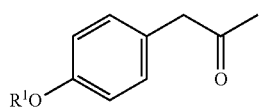

wherein $R^1$ includes $C_1$-$C_4$ alkyl with a compound of Formula

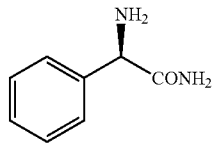

or an acid addition salt thereof, in the presence of cyanide ($CN^-$), to provide a product including the compound of Formula II or an acid addition salt thereof in at least about 55% diastereomeric purity. In some embodiments, $R^1$ is methyl. In some embodiments, the process also includes contacting the product including at least about 55% diastereomeric purity of the compound of Formula II or an acid addition salt thereof with a hydrolyzing agent selected from an acid, a base, a hydroperoxide, or an enzyme to provide a compound of Formula III:

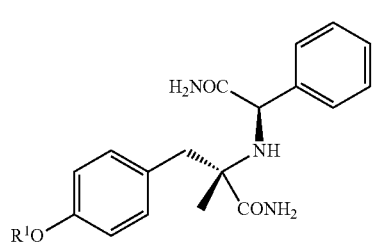

or an acid addition salt thereof in about 100% diastereomeric purity.

In some embodiments, the product precipitates from solution.

In some embodiments, the hydrolyzing agent includes a Brønsted acid.

In some embodiments, the process also includes hydrogenolyzing the compound of Formula III or an acid addition salt thereof to provide a compound of Formula V:

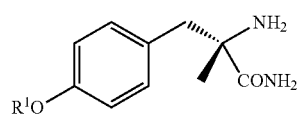

or an acid addition salt thereof.

In another aspect, a process is provided for the purification of a compound of Formula IV-A:

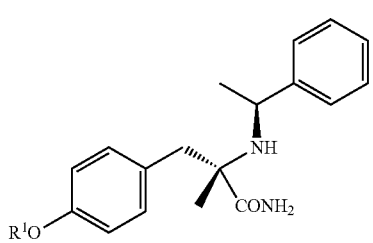

including re-crystallizing a mixture of diastereomers of Formula IV:

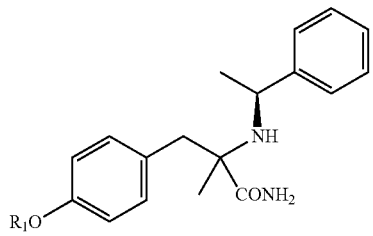

or acid addition salts thereof wherein $R^1$ includes $C_1$-$C_4$ alkyl to provide the compound of Formula IV-A in at least about 70% diastereomeric purity. In some embodiments, the re-crystallizing is performed using a solvent system including isobutyl alcohol. In some embodiments, $R^1$ is methyl.

In some embodiments, the process also includes hydrogenolyzing the compound of Formula IV-A or an acid addition salt thereof to provide a compound of Formula V:

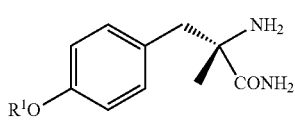

or an acid addition salt thereof. In some embodiments, the compound of Formula V or an acid addition salt thereof is at least about 80% enantiomeric purity after isolation.

In some embodiments, the process also includes contacting the compound of Formula V or an acid addition salt thereof with an acid to provide a compound of Formula

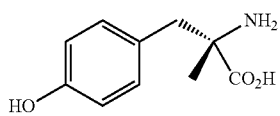

or an acid addition salt thereof.

In another aspect, a process is provided for the synthesis of a compound of Formula VIII:

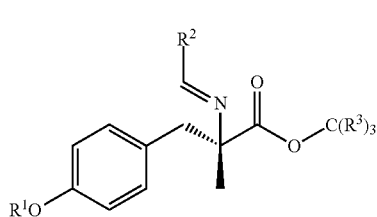

including contacting a compound of Formula VI:

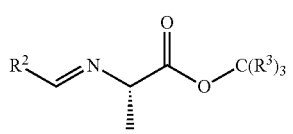

wherein $R^2$ includes substituted or unsubstituted aryl and each $R^3$ includes independently $C_1$-$C_3$ alkyl with O-allyl-N-benzylcinchonidinium bromide, a metal hydroxide, or a metal carbonate, and a compound of Formula VII:

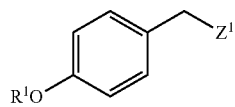

wherein $Z^1$ includes a leaving group and $R^1$ includes $C_1$-$C_4$ alkyl to provide a compound of Formula VIII in at least about 60% enantiomeric purity. In some embodiments, the compound provided is of Formula:

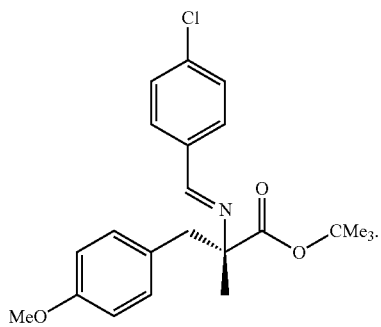

In some embodiments, the compound of Formula VII is 4-methoxybenzyliodide, 4-methoxybenzylbromide, or 4-methoxybenzylchloride.

In some embodiments, the process also includes contacting the compound of Formula VIII with a hydrolyzing agent to provide a compound of Formula IX:

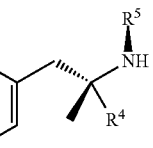

or an acid addition salt thereof. In some embodiments, the hydrolyzing agent includes a Brønsted acid.

In some embodiments, the process also includes contacting the compound of Formula IX or an acid addition salt thereof with an acid to provide the compound of Formula or a salt thereof. In some embodiments, the acid includes a Lewis acid.

In another aspect, an isolated stereoisomer of Formula X is provided:

or an acid addition salt thereof; wherein: $R^1$ includes $C_1$-$C_4$ alkyl; $R^4$ includes —CN or —$CONH_2$, $R^5$ is hydrogen or

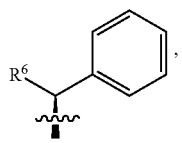

and $R^6$ is Me or —$CONH_2$ provided however that if $R^6$ is Me then $R^4$ is —$CONH_2$, and wherein the stereoisomer of Formula X is at least about 70% diastereomerically pure after isolation, provided however that if $R^5$ is H, then the stereoisomer of Formula X is at least about 50% enantiomerically pure after isolation.

In some embodiments, the compound of Formula X is a compound of Formula X-A or X-B or an acid addition salt of either of the following:

X-A

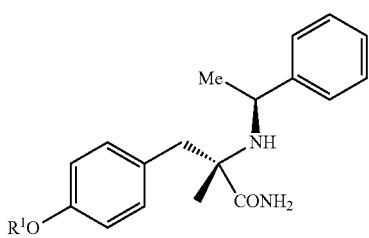

X-B

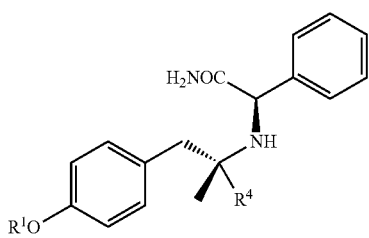

which is at least about 80% diastereomerically pure. In some embodiments, $R^1$ is methyl.

In some embodiments, the compound of Formula X is a compound of Formula V or an acid addition salt thereof:

V

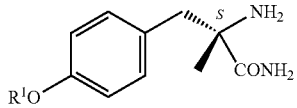

which is at least about 80% enantiomerically pure. In some embodiments, $R^1$ is methyl.

In another aspect, an isolated enantiomer of Formula XI is provided:

XI

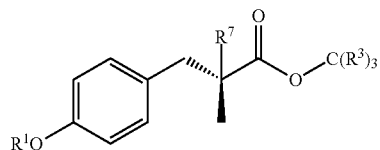

or an acid addition salt thereof; wherein: $R_1$ includes $C_1$-$C_4$ alkyl; $R_2$ includes unsubstituted or substituted aryl; each $R^3$ independently includes $C_1$-$C_3$ alkyl; and $R^7$ includes —$NH_2$ or

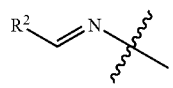

and wherein the enantiomer of Formula XI is at least about 60% enantiomerically pure after isolation.

In another aspect, an isolated enantiomer of Formula XI-A is provided:

XI-A

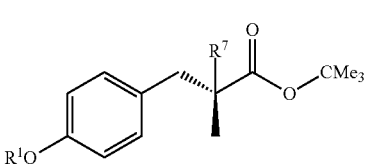

or an acid addition salt thereof.

In some embodiments, the isolated enantiomer Formula XI-B is provided:

XI-B

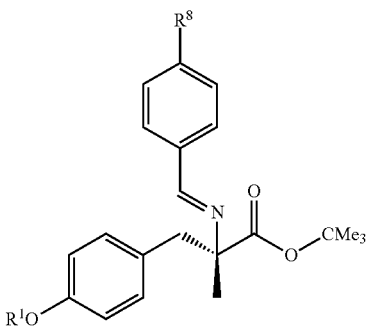

or an acid addition salt thereof wherein $R^8$ is halogen.

DETAILED DESCRIPTION

Definitions

The following definitions are provided to assist the reader. Unless otherwise defined, all terms of art, notations, and other scientific or medical terms or terminology used herein are intended to have the meanings commonly understood by those of skill in the chemical arts. In some cases, terms with commonly understood meanings are defined herein for clarity and/or for ready reference, and the inclusion of such definitions herein should not be construed as representing a substantial difference over the definition of the term as generally understood in the art.

"Acid" refers to a Brønsted acid or a Lewis acid.

"Alkyl" refers to a straight or branched chain alkyl group. "$C_1$-$C_4$ alkyl" refers to a substituted or unsubstituted straight or branched chain alkyl groups having 1-4 carbon atoms. $C_1$-$C_4$ alkyl groups include, for example, methyl, ethyl, propyl, isopropyl, n-butyl, isobutyl, and tert-butyl.

"Aryl" refers to a cyclic moiety that includes one or more monocyclic or fused ring aromatic systems. Such moieties include any moiety that has one or more monocyclic or bicyclic fused ring aromatic systems, including but not limited to phenyl and naphthyl.

"Brønsted Acid" refers to a compound that can donate a proton (H+). Examples of Brønsted acids include, without limitation, hydrochloric acid, hydrobromic acid, sulfuric acid, and various sulfonic acids.

"$(C_m-C_n)$", "$C_m-C_n$", or "$C_{m-n}$" refer to the number of carbon atoms in a certain group before which one of these symbols are placed. For example, $C_1-C_3$ alkyl refers to an alkyl group containing from 1 to 3 carbon atoms.

"Halogen" or halo" refers to, by themselves or as part of another substituent, unless otherwise stated, a fluorine, chlorine, bromine, or iodine atom.

"Hydrogenolyzing" refers to cleaving a heteroatom-benzylic or substituted benzylic (substituted on the phenyl and/or the methylene groups) bond by adding hydrogen and producing a heteroatom-H (such as an O—H, N—H, or S—H) moiety. Hydrogenolysis is a way to deprotect a protected amino, hydroxyl, carboxyl, or mercapto functionality. Various methods of hydrogenolyzing a nitrogen-benzylic or nitrogen-substituted benzylic moiety, are known to one of skill in the art and reported, for example, and without limitation, in Wuts et al., Greene's Protective Groups in Organic Synthesis, 4th Edition, 2006.

"Leaving group" refers to an atom or a group that can be replaced by a nucleophile. Examples of leaving groups include, but are not limited to, halide and sulfonate.

"Lewis acid" refers to a compound that can accept a lone electron pair. Examples of Lewis acids include, without limitation, $B(R^y)_3$ wherein each $R^y$ independently is halogen, alkyl, alkoxy, or aryl.

"Substituted" refers to a group as defined herein in which one or more bonds to a hydrogen are replaced by a bond to non-hydrogen "substituents" such as, but not limited to, acetyl, carboxylic acid or carboxylate ester, halogen atom, trifluoromethyl, methoxy, and —$NH_2$ and its mono and dialkylated derivatives. Aryl groups may also be substituted with alkyl or substituted alkyl groups.

"Sulfonate" refers to a group of Formula —$OSO_2R^x$ wherein $R^x$ is alkyl, trifluoromethyl, or substituted or unsubstituted aryl.

In one aspect, isolated stereoisomers of Formula X are provided:

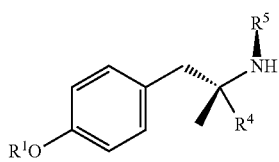

X or a salt thereof; where $R^1$ is $C_1-C_4$ alkyl; $R^4$ is —CN or —$CONH_2$; $R^5$ is hydrogen or

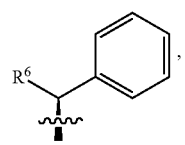

and $R^6$ is Me or —$CONH_2$, provided that when $R^6$ is Me $R^4$ is —$CONH_2$, and where the isolated stereoisomer of Formula X is greater than 50% diastereomerically pure; and further provided that where $R^5$ is H the isolated stereoisomer of Formula X is greater than 50% enantiomerically pure. In one embodiment, $R^1$ is Me.

In one embodiment, the isolated stereoisomer is a compound represented Formula X-D:

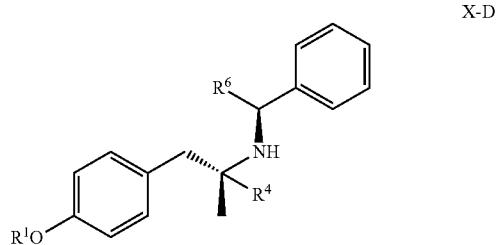

X-D where $R^1$, $R^4$, and $R^6$ are as defined for Formula X, above. In some embodiments, a composition is provided including the isolated stereoisomer of Formula X-D in at least about 75% diastereomeric purity. In some such embodiments, this includes providing the isolated stereoisomer of Formula X-D in at least about 80%, at least about 85%, at least about 90%, at least about 98%, or at least about 99% diastereomeric purity. In another embodiment, $R^6$ is Me. In another embodiment, $R^6$ is —$CONH_2$. In another embodiment, $R^1$ is Me.

In another embodiment, the isolated diastereomers of Formula X-A and X-B are provided:

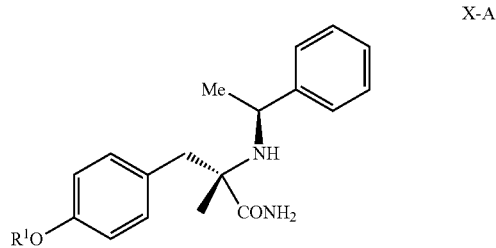

X-A

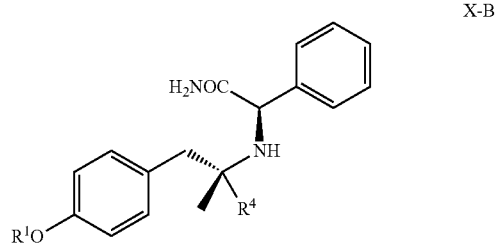

X-B wherein $R^1$ and $R^4$ are defined as in Formula X above, in at least 80% diastereomerically pure form. In another embodiment, $R^1$ is Me. In another embodiment, the isolated diastereomer is X-A and it is at least about 75% diastereomerically pure. In some such embodiments, the isolated diastereomer is X-A and it is at least about 80%, at least about 85%, at least about 90%, at least about 98%, or at least about 99% diastereomerically pure. In another embodiment, the isolated diastereomer is X-B and it is at least about 55% diastereomerically pure. In some embodiments, the isolated diastereomer X-B is at least about 60%, at least about 70%, at least about 75%, at least about 80%, at least about 85%, at least about 90%, at least about 98%, or at least about 99% diastereomerically pure.

In another embodiment, the isolated diastereomer is of Formula II:

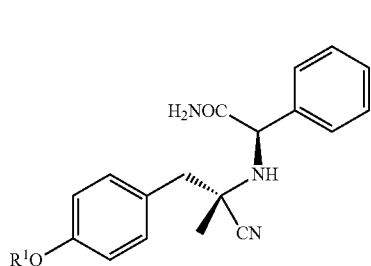

II

In another embodiment, the isolated diastereomer is of Formula III:

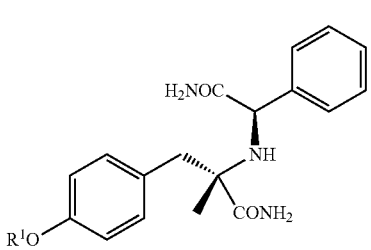

III

In certain embodiments, $R^1$ is Me.

As used here, "diastereomerically pure" refers to the mole % of a certain diastereomer in a mixture of such diastereomers. For example, and without limitation, where the compound of Formula X-A is provided in about 80% diastereomerically pure form, it may also include about 20% of the diastereomer of Formula X-E:

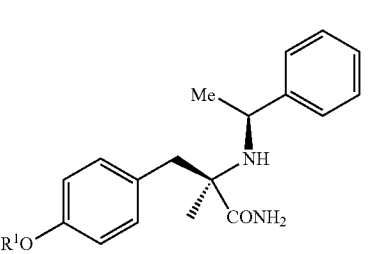

X-E

In this example, the diastereomeric excess (or "de") of the X-A diastereomer in the mixture of diastereomers is about (80-20)% or about 60%.

Similarly, for example, and without limitation, the compound of Formula X-B may be provided in about 80% diastereomerically pure form, which includes about 20% of the diastereomer having Formula X-F:

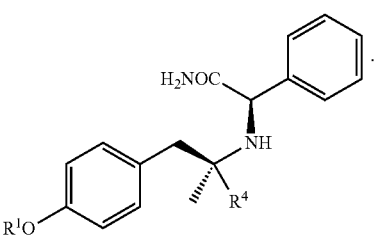

X-F

Similarly, for example, and without limitation, a compound of Formula X-D which is about p % diastereomerically pure, includes about (100−p)% of a diastereomer of Formula, X-G:

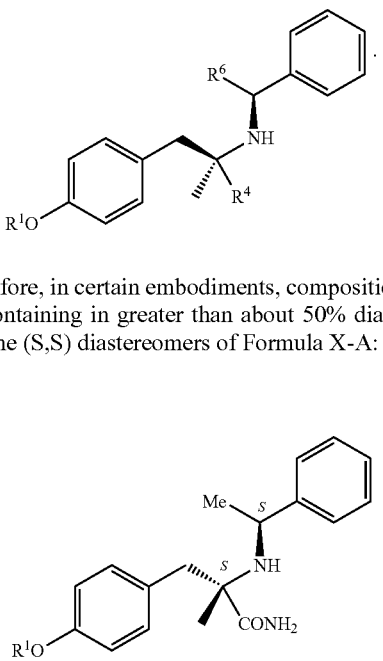

X-G

Therefore, in certain embodiments, compositions are provided containing in greater than about 50% diastereomeric purity, the (S,S) diastereomers of Formula X-A:

X-A

Also, in certain embodiments, compositions are provided containing in greater than about 50% diastereomeric purity, the (S,R) diastereomers of Formula X-B:

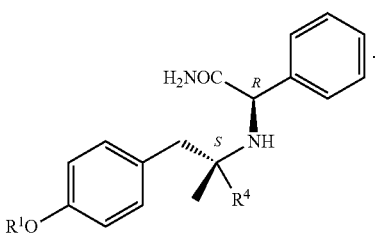

X-B

In a certain embodiment, $R^4$ is —$CONH_2$. In certain other embodiments, $R^1$ is methyl.

In another embodiment, an isolated S-enantiomer of Formula V is provided:

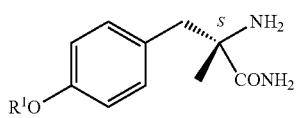

V in at least about 75% to at least about 80% enantiomerically pure form. In another embodiment, the isolated enantiomer of Formula V is provided in at least about 85%, at least about 90%, at least about 98%, or at least about 99% enantiomerically pure form. In another embodiment, a composition is provided including at least about 75% of the compound of Formula V, which is the S-enantiomer. In certain embodiments within these embodiments, $R^1$ is methyl.

As used here, enantiomerically pure refers to the mole % of a certain enantiomer in a mixture of such enantiomers. The rest of the isolated composition may, for example and without limitation, substantially, be the other enantiomer. For example, and without limitation, the compositions containing about 80% of the S enantiomer of Formula V provided in an embodiment of the present technology, includes, about 20% of the R-enantiomer of Formula V-A:

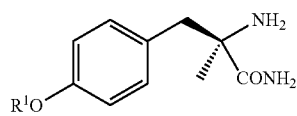

V-A

In this example, the enantiomeric excess (or "ee") of the V enantiomer in the mixture of enantiomers is about 60%.

In another aspect, an isolated S-enantiomer of Formula XI is provided:

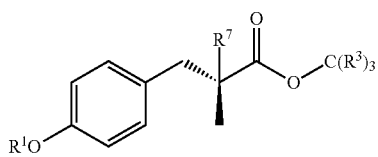

XI or a salt thereof where $R_1$ is $C_1$-$C_4$ alkyl; $R^7$ is —$NH_2$ or

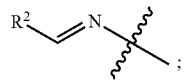

;

$R_2$ is unsubstituted or substituted aryl, and each $R^3$ independently is $C_1$-$C_3$ alkyl, and wherein the isolated S-enantiomer of Formula XI is greater than 60% enantiomerically pure. In another embodiment, the isolated enantiomer is of Formula XI-A:

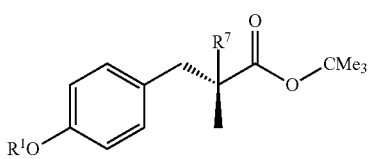

XI-A or a salt thereof. In another embodiment, the isolated enantiomer is of Formula XI-B:

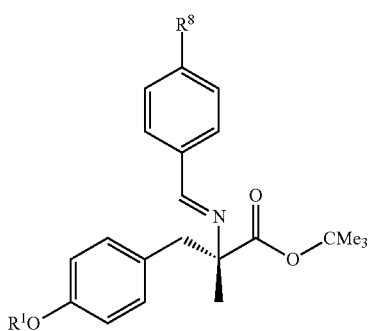

XI-B or a salt thereof wherein $R^8$ is halo. In certain embodiments, $R^1$ is Me. In another embodiment the isolated enantiomers are of Formulas:

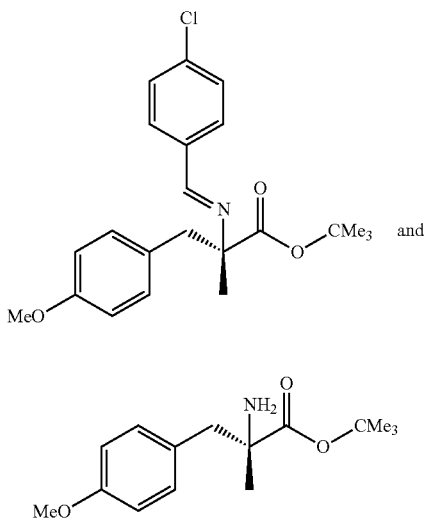

and or salts thereof.

The various isolated diastereomers, and isolated enantiomers, and compositions including them, are prepared according to processes provided in other aspects and embodiments of the present technology, and using certain processes which are well known to one of skill in the art. For example, and without limitation, see Schemes 1 and 2 below. The various diastereomers and enantiomers may be isolated in a number of ways including, but not limited to, crystallization, chromatographic separation, precipitation, and combinations thereof, as also described herein below and/or known to one of skill in the art. The determination of diastereomeric or enantiomeric purity and the diastereomeric or enantiomeric excess of an isolated composition containing a mixture of diastereomers or enantiomers is performed by using a number of methods including, but not limited to, NMR (with or without chiral resolving agents, as appropriate), chromatography (using chiral columns for determining enantiomeric purity), polarimetry, and circular dichroism.

Scheme 1

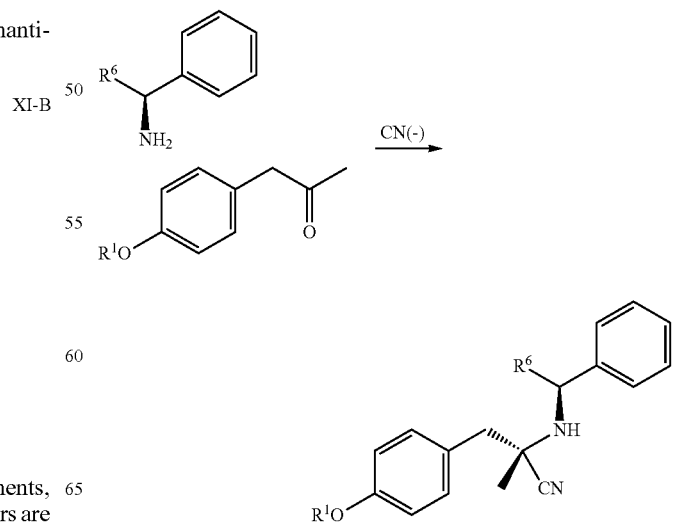

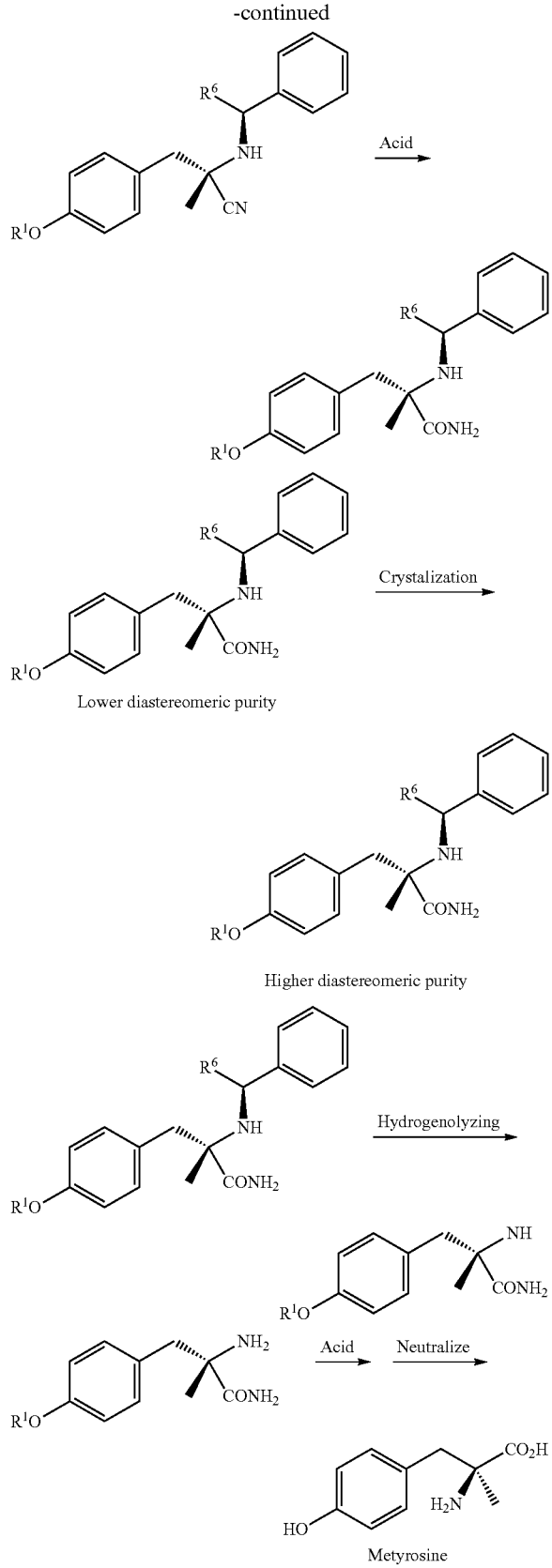

An acid salt of the starting material of each step may also be used for certain of the transformations shown in Scheme 1.

In one aspect, a process is provided for the synthesis of a compound of Formula II:

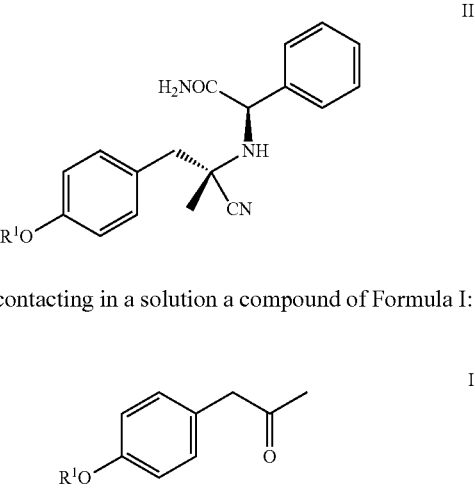

including contacting in a solution a compound of Formula I:

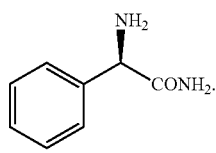

wherein $R^1$ is $C_1$-$C_4$ alkyl with (R)-phenylglycinamide or an acid salt thereof, in the presence of cyanide (CN) to provide a precipitate which includes the compound of Formula II in at least about 55% diastereomeric purity. (R)-phenylglycinamide is represented as:

In another embodiment, the precipitate includes at least about 60%, at least about 65%, at least about 70%, at least about 75%, at least about 80%, at least about 85%, at least about 90%, at least about 95%, or at least about 98% of the compound of Formula II. In another embodiment, the precipitate includes the compound of Formula II in at least about 60%, at least about 65%, at least about 70%, about 75%, at least about 80%, at least at least about 85%, at least about 90%, at least about 95%, or at least about 98% diastereomeric purity. Thus, in certain embodiments, processes are provided for the synthesis of a compound of Formula II in a substantially diastereomerically pure form. In some embodiments, the cyanide source is an alkali metal cyanide such as KCN or NaCN.

In one embodiment, the contacting is performed at about 15° C. to about 60° C. In other embodiments, the contacting may also be performed at lower temperatures, wherein, the time period of the contacting may be of longer duration than those at 15° C. or higher. In another embodiment, the solution is an aqueous solution. In another embodiment, the aqueous solution further includes a lower alkanol. In another embodiment, the lower alkanol is methanol. In another embodiment, the contacting is performed for about 5 h to about 20 days, about 10 h to about 10 days, about 20 h to about 5 days, and about 2 days to about 4 days. In one embodiment, the precipitate is collected by filtration. Volatiles may be removed from the collected precipitate in vacuo. In one embodiment, $R^1$ is methyl.

In another embodiment, the process may also include contacting the precipitate including the compound of Formula II or an acid salt thereof, with a hydrolyzing agent to provide an isolated compound of Formula III:

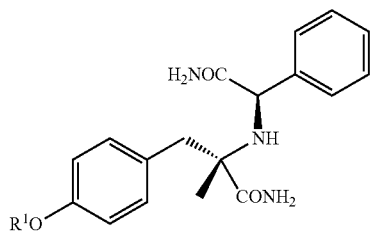

III or an acid salt thereof in substantial diastereomeric purity. In another embodiment, the hydrolyzing agent is an acid, a base, a hydroperoxide, or an enzyme. In other embodiments, the hydrolyzing agent may include an oxidizing agent. In one embodiment, the acid is a Brønsted acid. In another embodiment, the Brønsted acid is sulfuric acid. In another embodiment, the sulfuric acid contains up to 10% weight/weight water. In another embodiment, the Brønsted acid is a sulfonic acid, hydrogen halide, or a carboxylic acid. In another embodiment, the Brønsted acid is $CF_3SO_3H$, HCl, polyphosphoric acid, or HOAc. In another embodiment, the Lewis acid is $Al_2O_3$, $BF_3$, or $TiCl_4$. In another embodiment, the contacting is performed at a temperature of about −25° C. to about 5° C. In one embodiment, the contacting is performed in a solution. A variety of solvent systems may be used for preparing the solution. In one embodiment, the solvent system includes a chlorinated solvent. In another embodiment, the chlorinated solvent is dichloromethane. Other steps, well known to one of skill in the art, such as neutralization, separation of organic and aqueous phases, and isolation of the product, are also performed as needed during the above preparation, as will be apparent to one of skill in the art upon reading this disclosure in its entirety. In another embodiment, the compound of Formula III is obtained in a diastereomeric purity of at least 80%. In another embodiment, the compound of Formula III is isolated in a composition including at least 80% of the compound of Formula III. In another embodiment, $R^1$ is methyl.

In another embodiment, the process further includes increasing the diastereomeric excess of the compound of Formula III in a diastereomeric mixture by crystallization. In one embodiment, diastereomers of Formula

III-A

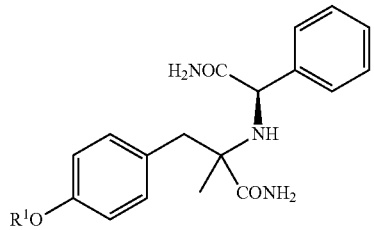

are crystallized to provide the isolated diastereomer of Formula

III

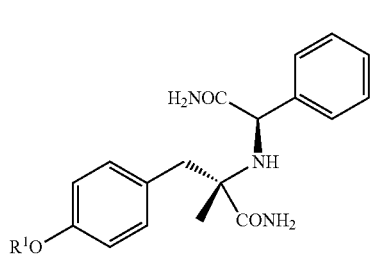

or acid salts thereof in substantial diastereomeric purity.

In one embodiment, the crystallizing is performed by dissolving the compound of Formula III in a solvent system including a ketone. In one embodiment, the ketone is methyl isobutyl ketone. Other solvent systems may include an aromatic solvent, a lower alkanol, or an ether. In other embodiments, the solvent system includes toluene, isopropyl alcohol, or isobutyl alcohol. In another embodiment, the dissolving is performed by dissolving the compound in a refluxing solvent. In another embodiment, the dissolved solution is concentrated before the substantially diastereomerically pure compound of Formula III separates as a solid from the solution. The process of crystallization may be repeated more than once, for example and without limitation, up to 10 times to provide the compound of Formula III in high diastereomeric purity (or in high diastereomeric excess, or de). In another embodiment, $R^1$ is methyl.

In another aspect, the present technology provides a process for the purification of a compound of Formula IV-A or an acid salt thereof:

IV-A

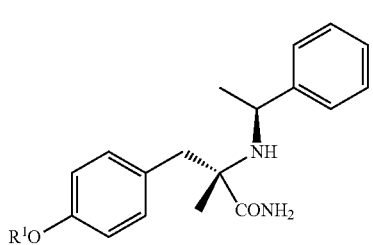

including crystallizing a mixture of diastereomers of Formula IV or acid salts thereof:

IV

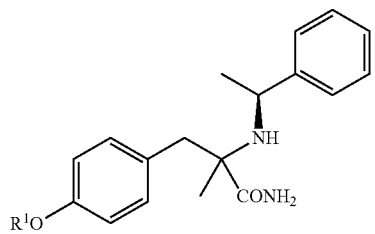

wherein $R^1$ is $C_1$-$C_4$ alkyl to provide the crystallized compound of Formula IV-A or an acid salt thereof in at least about 70% diastereomeric purity. The diastereomers represented by Formula IV or salts thereof are essentially diastereomeric compounds of Formula IV-A and Formula IV-B or salts thereof:

IV-B

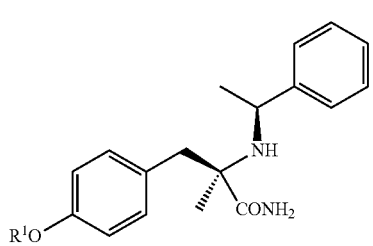

In certain embodiments, the mixture of diastereomers of Formula IV includes the diastereomer of Formula IV-A in about 50%, about 55%, about 60%, about 65%, about 70%, diastereomeric purity. Diastereomeric mixtures of Formula IV including the diastereomer of Formula IV-A in more than 50% diastereomeric purity, may also be purified in accordance with the processes described herein. In another embodiment, the crystallizing is performed using a solvent system including isobutyl alcohol. In another embodiment, the solvent system includes isopropyl alcohol. In another embodiment, the solvent system includes methyl isobutyl ketone. In another embodiment, the solvent system includes isopropyl alcohol and methyl isobutyl ketone. In another embodiment, $R^1$ is Me. The process of crystallization may be repeated more than once, for example and without limitation, up to 10 times, to provide the compound of Formula IV-A in high diastereomeric purity (or in high "de").

In another embodiment, the present technology provides a process including hydrogenolyzing the compound of Formula III and IV-A of substantial diastereomeric purity as provided in various aspects and embodiments of the present technology or acid salts thereof to provide a compound of Formula V:

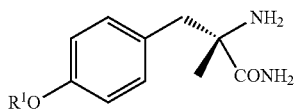

V or an acid salt thereof in substantial enantiomeric purity. In one embodiment, the hydrogenolyzing is performed using catalytic hydrogenation. Catalytic hydrogenation is performed using hydrogen and a suitable Pd catalyst. In another embodiment, the palladium catalyst is Pd/C (Pd on charcoal). In one embodiment, the Pd catalyst includes water. In another embodiment, the hydrogenolyzing is performed by transfer hydrogenation wherein, during catalytic hydrogenation, a compound other than molecular hydrogen is employed as the source of hydrogen. In another embodiment, the molecule other than hydrogen thus employed is formic acid or a formate salt. In another embodiment, the hydrogenolyzing was performed essentially using $HCO_2H$ or $NH_4HCO_2$ and a Pd catalyst. In another embodiment, the Pd catalyst is Pd/C. In another embodiment, the process further includes performing the hydrogenolyzing in a solvent system. In another embodiment, the solvent system includes a lower alkanol. In another embodiment, the lower alkanol is EtOH. Other methods of hydrogenolyzing may be employed in accordance with the various process embodiments of the present technology, upon reading this disclosure in its entirety. In another embodiment, the compound of Formula V provided is isolated in at least about 80% enantiomeric purity. In another embodiment, $R^1$ is methyl.

In another embodiment, a process is provided which includes contacting the compound of Formula V with an acid to provide metyrosine, which has a Formula:

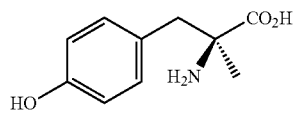

or a salt thereof. In another embodiment, the acid is a Lewis acid. In another embodiment, the Lewis acid is a trivalent boron based Lewis acid. In another embodiment, the trivalent boron based Lewis acid is $BBr_3$.

Certain other compounds and processes to make them are schematically described below.

Scheme 2

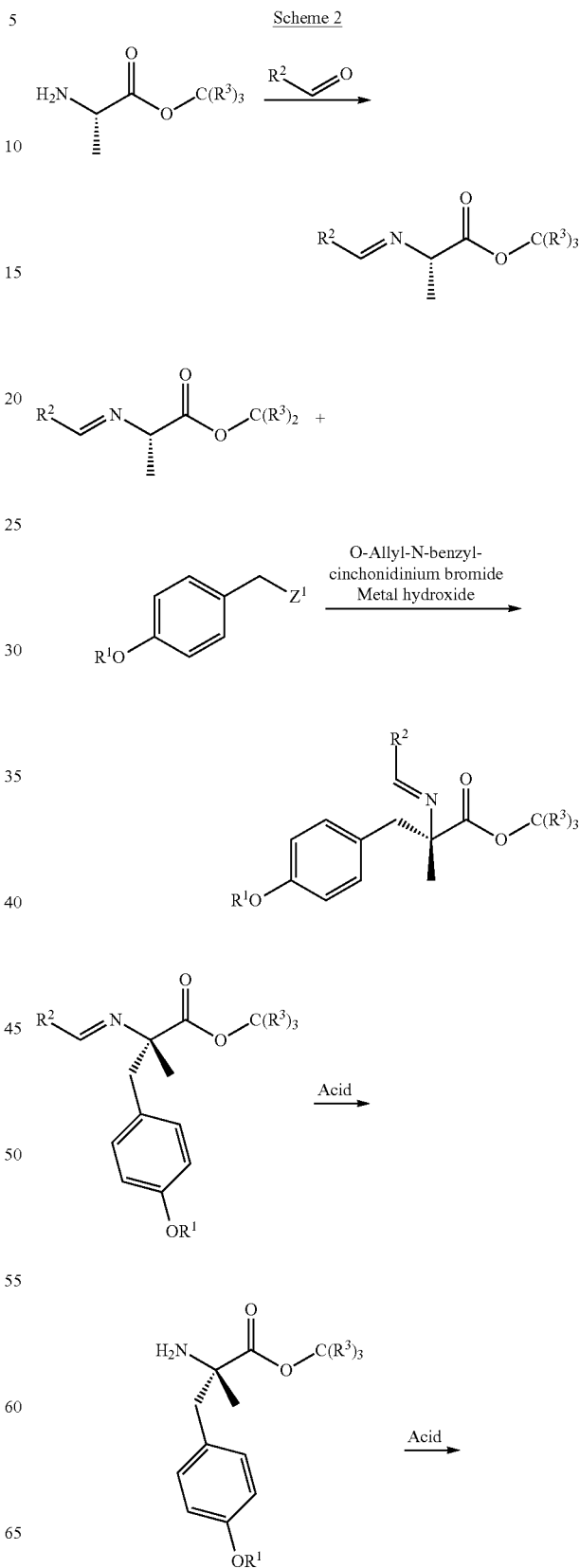

-continued

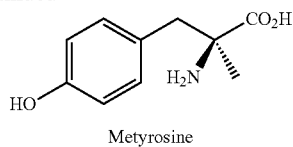
Metyrosine

Thus, in another aspect, the present technology provides a process for the synthesis of a compound of Formula VIII:

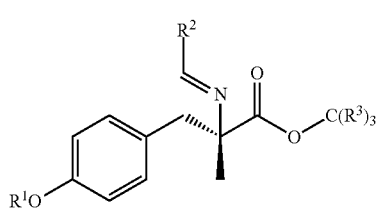
VIII including contacting a compound of Formula VI:

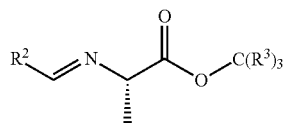
VI wherein $R^2$ is substituted or unsubstituted aryl and each $R^3$ is independently $C_1$-$C_3$ alkyl with O-allyl-N-benzylcinchonidinium bromide, a base including a metal hydroxide or a metal carbonate, and a compound of Formula VII:

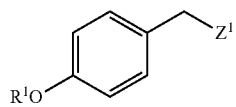
VII wherein $Z^1$ is a leaving group and $R^1$ is $C_1$-$C_4$ alkyl to provide a compound of Formula VIII isolated in at least 60% enantiomeric purity (enantiomeric excess or ee of 20%).

In one embodiment, the contacting is performed at contacting temperatures of about 5° C., about 0° C., and about −5° C. In another embodiment, after the contacting, the temperature may be raised to a temperature above the contacting temperature. In another embodiment, the contacting is performed in a solvent system including an aromatic solvent. In another embodiment, the aromatic solvent is toluene. In another embodiment, $R^1$ is methyl. Other steps, well known to one of skill in the art, including, but not limited to, neutralization of reaction mixtures, separation of organic and aqueous phases, and isolation of the product, are also performed as needed as will be apparent to one of skill in the art upon reading this disclosure in its entirety.

In another embodiment, the compound provided is of Formula XI-B:

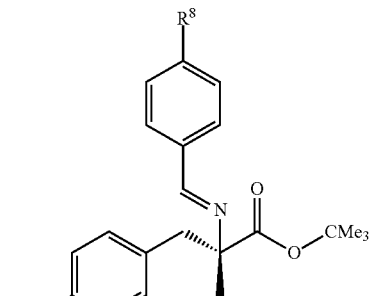
XI-B or a salt thereof wherein $R^8$ is a halogen. In another embodiment, $R^1$ is methyl. In another embodiment, the compound provided is of Formula:

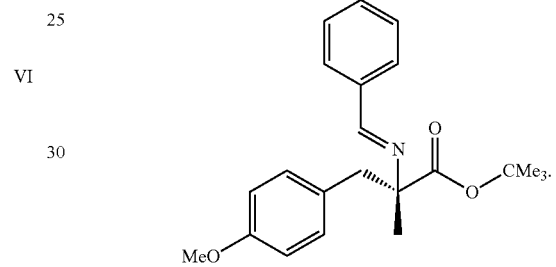

In another embodiment, the compound of Formula VII is 4-methoxybenzyliodide, 4-methoxybenzylbromide, or 4-methoxybenzylchloride.

In another embodiment, the process also includes contacting the compound of Formula VIII with an acid to provide a compound of Formula IX:

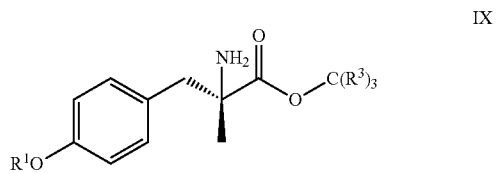
IX or an acid salt thereof. In one embodiment, the acid contacted is a Brønsted acid. In another embodiment, the Brønsted acid is hydrochloric acid. In another embodiment, $R^1$ is methyl.

In another embodiment, the process further includes contacting the compound of Formula VIII with an acid to provide metyrosine or a salt thereof in substantial enantiomeric purity. In another embodiment, the acid is a Brønsted acid. In another embodiment, the Brønsted acid is HBr. In another embodiment, the acid is a Lewis acid. In another embodiment, the Lewis acid is $BBr_3$.

In another embodiment, the process further includes contacting the compound of Formula IX with an acid to provide the compound of Formula

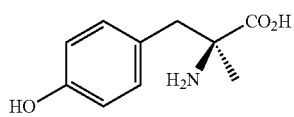

or a salt thereof in substantial enantiomeric purity. In one embodiment, the acid is a Lewis acid. In another embodiment, the Lewis acid is BBr$_3$.

In addition to the processes provided as certain aspects and embodiments of the present technology, steps well known to one of skill in the art, such as, neutralization, separation of organic and aqueous phases, and isolation of the product, may also be performed for preparing the compounds as described above, and will be apparent to one of skill in the art upon reading this disclosure in its entirety.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The present invention, thus generally described, will be understood more readily by reference to the following examples, which are provided by way of illustration and are not intended to be limiting of the present invention.

EXAMPLES

The following abbreviations are used in the examples:

| | |
|---|---|
| [α] | Specific rotation |
| AUC | Area under curve |
| BINOL | 1,2-Bi-2-naphthol |
| DMSO | Dimethyl sulfoxide |
| dr | Diastereomeric ratio |
| ESI | Electrospray ionization |
| HPLC | high performance liquid chromatography |
| iBu | Isobutyl |
| IPA | Isopropyl alcohol |
| iPr | Isopropyl |
| Me | Methyl |
| MHz | Mega hertz |
| MIK | Methyl isobutyl ketone |
| MS | Mass spectrometry |
| MTBE | Methyl tertiary butyl ether |
| mM | Milli molar |
| mmol | Milli mole |
| NMR | Nuclear magnetic resonance |
| Pd/C | Palladium on charcoal |
| R and/or S | Used to denote the stereochemistry of a chiral center according to the Cahn Ingold Prelog priority rules |
| t$_R$ | Retention time |

Preparation of metyrosine using (R)-phenylglycinamide is illustrated in Examples 1-6 below Example 1

(R)-Phenylglycinamide.HCl

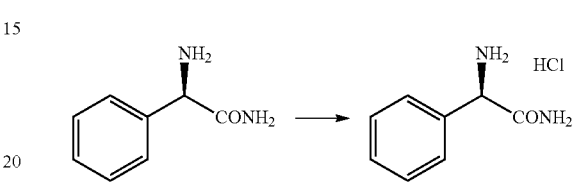

To a 500 mL flask were charged (R)-phenylglycinamide (20.0 g, 133 mmol, 1 eq. Amplachem ref: Aa-33365) and MeOH (160 mL). 4 M HCl/dioxane (50 mL, 200 mmol, 1.5 eq.) was then added dropwise resulting in the formation of a white precipitate. The mixture was stirred for 30 min, was filtered and was washed with MeOH (20 mL) and diethyl ether (20 mL). Drying in vacuo provided (R)-phenylglycinamide.HCl (21.9 g, 89%) as a white solid. $^1$H NMR (D$_2$O, 400 MHz) 4.97 (s, 1H); 7.36-7.41 (m, 5H).

Example 2

2-[1-(S)-Cyano-2-(4-methoxyphenyl)-1-methylethylamino]-2-(R)-phenylacetamide 2

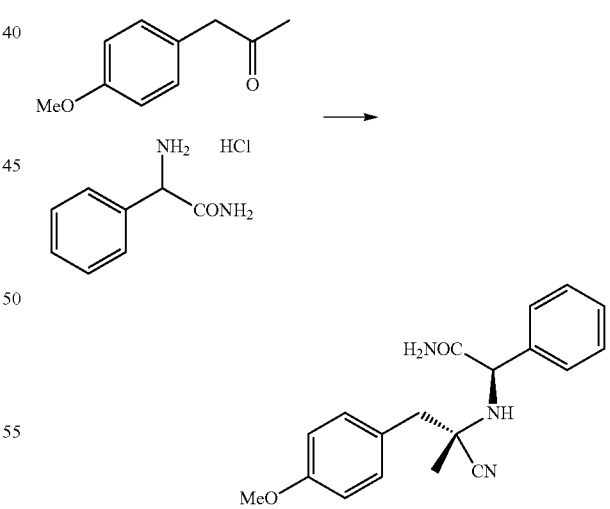

Method A.

To a 500 mL flask were charged (R)-phenylglycinamide-.HCl (15.0 g, 80.6 mmol, 1 eq.), MeOH (104 mL), H$_2$O (17 mL) and p-methoxyphenylacetone (12.4 mL, 80.6 mmol, 1 eq, Aldrich, ref: 19917-6). To this mixture was added a solution of NaCN (3.95 g, 80.6 mmol, 1 eq.) in H$_2$O (10 mL). The resulting solution was stirred for 4 days at room temperature while a white precipitate formed. The precipitate was filtered and washed with H₂O/MeOH (7:3) to provide 2-[1-(S)-cyano-2-(4-methoxyphenyl)-1-methylethylamino]-2-(R)-phenylacetamide 2 (11.0 g) as a white solid. The filtrate was stirred for 3 d more at room temperature and the solid formed was filtered to provide 2 (3.30 g). The filtrate was stirred for 1 d more to provide 2 (1.70 g). The filtered solids were combined and dried in vacuo to provide 2 (16.0 g, 61%, dr 98/2) as a white solid.

Method B.

In a sealed tube were charged (R)-phenylglycinamide.HCl (1.2 g, 6.45 mmol, 1 eq.), MeOH (4 mL), H₂O (7 mL) and p-methoxyphenylacetone (991 μL, 6.45 mmol, 1 eq.). A solution of NaCN (316 mg, 6.45 mmol, 1 eq.) in H₂O (1 mL) was added. The mixture was stirred for 20 hours at 40° C. resulting in the formation of a white precipitate. The precipitate was filtered, was washed with H₂O/MeOH (7:3 v/v, 2×2 mL) and was dried in vacuo to provide 2 (1.59 g, 76%, dr 98/2) as a white solid. $^1$H NMR (CDCl₃, 400 MHz) 1.14 (s, 3H); 2.90 (d, J=13.6 Hz, 1H); 2.99 (d, J=13.6 Hz, 1H); 3.20 (bs, 1H); 3.80 (s, 3H); 4.51 (s, 1H); 5.45 (bs, 1H); 5.75 (bs, 1H); 6.90 (d, J=8.6 Hz, 2H); 7.27 (d, J=8.6 Hz, 2H); 7.30-7.50 (m, 5H). dr determination: $^1$H NMR comparing integration of peaks of 2 at 2.90/2.99 (1.98H, formally 2H) with those of its diastereoisomer or diastereomer (prepared from racemic phenylglycinamide) at 2.82/2.85 (0.04H, formally 2H). $^1$H NMR diastereoisomer of 2 (CDCl₃, 400 MHz) 1.49 (s, 3H); 2.82 (d, J=13.8 Hz, 1H); 2.85 (d, J=13.8 Hz, 1H); 3.78 (s, 3H); 4.52 (s, 1H); 5.55 (bs, 1H); 6.60 (bs, 1H); 6.84 (d, J=8.6 Hz, 2H); 7.17 (d, J=8.6 Hz, 2H); 7.30-7.40 (m, 5H).

Example 3

2-[(R)-(Carbamoylphenylmethyl)-amino]-3-(4-methoxyphenyl)-2-(S)-methylpropionamide 3

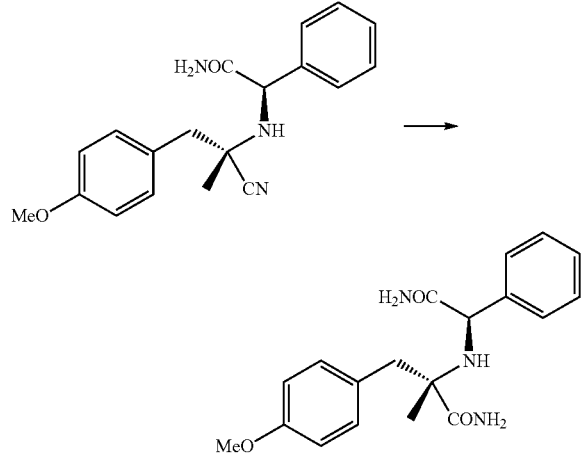

To a 500 mL flask were added nitrile 2 (10.0 g, 30.95 mmol) and CH₂Cl₂ (130 mL). The solution was cooled to −10° C. and H₂SO₄ (10 mL) was added dropwise over 15 min. The mixture was stirred for 2 h at 0° C. Ice (200 g) was added and the mixture was stirred for 1 h. The mixture was basified with 32% aq NH₃ to pH 8-9, EtOAc (400 mL) was added and the phases were separated. The aqueous phase was extracted with EtOAc (2×250 mL). The combined organic phases were dried over MgSO₄ and were concentrated to provide 3 (11.1 g (9.99 g theoretical, the sample contains 10% w/w of EtOAc by NMR) 94%, 92.9% chemical purity, 97% de by HPLC/MS) as a white solid. HPLC/MS $t_R$=3.04 min; m/z=342.1 (M+1)

de determination: HPLC/MS comparing integration of peaks at $t_R$=3.04 min (98.5 area %) and $t_R$=2.92 min (1.5 area % the other diastereoisomer of 3) HPLC/MS diastereoisomer of 3 $t_R$=2.92 min; m/z=342.1 (M+1)

Example 4

Purification of 3 by Crystallization

Amide 3 (8.10 g, 23.7 mmol) and methyl isobutyl ketone (124 mL) were heated to reflux temperature until the solid was dissolved and the solution was cooled to room temperature. The solid formed was filtered, was washed with methyl isobutyl ketone (2×20 mL) and was dried in vacuo to provide 3 (5.45 g, 67%, >99.5% purity by HPLC/MS) as a white solid. $^1$H NMR (DMSO, 200 MHz) 1.00 (3H, s); 2.35 (bs, 1H); 2.75 (d, J=13.3 Hz, 1H) 2.85 (d, J=13.3 Hz, 1H); 3.61 (s, 3H); 4.17 (s, 1H); 6.60 (d, J=8.4 Hz, 2H); 691 (d, J=8.4 Hz, 2H); 6.93 (bs, 1H), 7.01 bs (1H); 7.20-7.50 (m, 6H); 7.6 (bs, 1H). HPLC/MS m/z=342.1 (M+1)

Example 5

2-(S)-Amino-3-(4-methoxyphenyl)-2-methylpropionamide 4

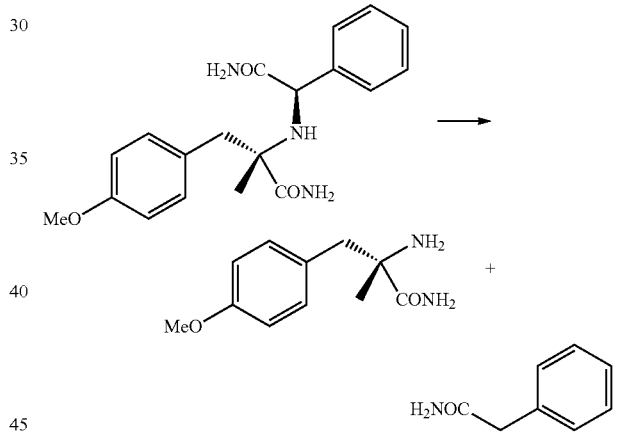

Method A, Hydrogenolysis: Amine 3 (6.00 g, 17.6 mmol, 1 eq) was dissolved in MeOH (60 mL) and 10% Pd/C (2.15 g, 56% moisture content, 16 wt %) was added. The mixture was stirred under H₂ (3 bar) at 50° C. for 16 h. The mixture was filtered through Celite, the filter pad was washed with MeOH (20 mL) and the filtrates were concentrated to provide 5.50 g of a 1:1 mixture of 4 (3.37 g, 91%) and phenylacetamide as a white solid.

Method B, Transfer hydrogenolysis: Amine 3 (500 mg, 1.47 mmol, 1 eq) was dissolved in i-PrOH (5 mL) under Argon. 10% Pd/C (200 mg, 56% moisture content, 18 wt %) and ammonium formate (601 mg, 9.56 mmol, 6.5 eq.) were added. The mixture was stirred at reflux temperature for 1 h. The mixture was filtered through Celite, the filter pad was washed with EtOH (10 mL) and the filtrates were concentrated to provide 480 mg of a 1:1 mixture of desired compound (293 mg, 96%) and phenylacetamide as a white solid. $^1$H NMR (DMSO, 400 MHz) 1.14 (s, 3H); 2.10 (bs, 2H); 2.50 (d, J=13.1 Hz, 1H); 2.95 (d, J=13.1 Hz, 1H); 3.69 (s, 3H); 6.80 (d, J=8.5 Hz, 2H); 6.81 (bs, 1H); 6.90 (bs, 1H); 7.09 (d, J=8.5 Hz, 2H). (Phenylacetamide 3.34 (s, 2H); 7.15-7.28 (m, 6H);

7.42 (bs, 1H).). HPLC/MS 4 $t_R$=1.96 min. MS (ESI (+)) m/z=164.2 (M-CONH$_2$). (Phenylacetamide $t_R$=1.76 min. MS (ESI (+)) m/z=136.2 (M+1)).

Example 6

Metyrosine 1

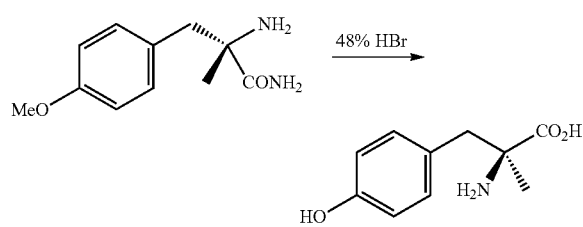

To a 100 mL flask with a reflux condenser was charged amide 4 (5.50 g of a mixture containing 4 (3.37 g, 16.1 mmol) and phenylacetamide (2.13 g)) and 48% HBr (30 mL). The solution was heated for 5 h at 120° C. and was cooled to room temperature. H$_2$O (60 mL) was added and the solution was washed with EtOAc (3×35 mL). The aqueous phase was concentrated in vacuo to provide a beige paste. The paste was dissolved in H$_2$O (15 mL) and the resulting mixture was heated to 65° C. Activated carbon (300 mg, Type NORIT SX) was added and the mixture was stirred for 15 min, was filtered and the filter pad was washed with water (2×4 mL). The combined filtrates were heated to 55° C. and the pH was adjusted to 5-6 using 32% aq. NH$_3$. The mixture was cooled to 0° C., was stirred for 15 min and was filtered. The collected solids were washed with cold water (2×5 mL) and were dried in vacuo to provide (−)-α-methyl-L-tyrosine (or metyrosine) 1 (2.65 g, 84%) as a white solid. HPLC (Zorbax C18, NaH$_2$PO$_4$ 10 mM pH=3/MeCN (100:0) 10 min, (100:0) to (0:100) 15 min, 0:100 5 min) $t_R$=10.1 min. Chiral HPLC (Nucleosil Chiral-1, CuSO$_4$ 10 mM/MeCN 10:1) $t_R$=16.9 min. m.p.=320-321° C. [α]$_{546}$=+201° (c=0.5 Copper complex solution) (lit.[2]+185-190° Copper complex solution preparation: Solution A (anhydrous NaOAc dissolved in H$_2$O (150 mL) in 250 mL volumetric flask, glacial acetic acid (50 mL) added and diluted to volume with H$_2$O) mixed with Solution B (cupric sulfate (62.5 g) diluted to volume with H$_2$O in a 200 mL volumetric flask) in a 1 L volumetric flask and was diluted to volume with H$_2$O. Metyrosine solution (5 mg/mL) was prepared in this solution.

To obtain an NMR spectrum (taking into account the low solubility of the product), a small sample (10 mg) was transformed into its HCl salt. The sample was dissolved in 2 M HCl and the solution was evaporated to dryness. $^1$H NMR (D$_2$O, 400 MHz) 1.49 (s, 3H); 2.90 (d, J=14.5 Hz, 1H); 3.16 (d, J=14.5 Hz, 1H); 6.75 (d, J=8.2 Hz, 2H), 7.01 ((d, J=8.2 Hz, 2H). $^{13}$C NMR (D$_2$O, 100.6 MHz) 21.6; 41.6; 61.0; 116.0, 125.0; 131.7; 155.5; 173.8.

Preparation of Metyrosine using (S)-phenylethylamine

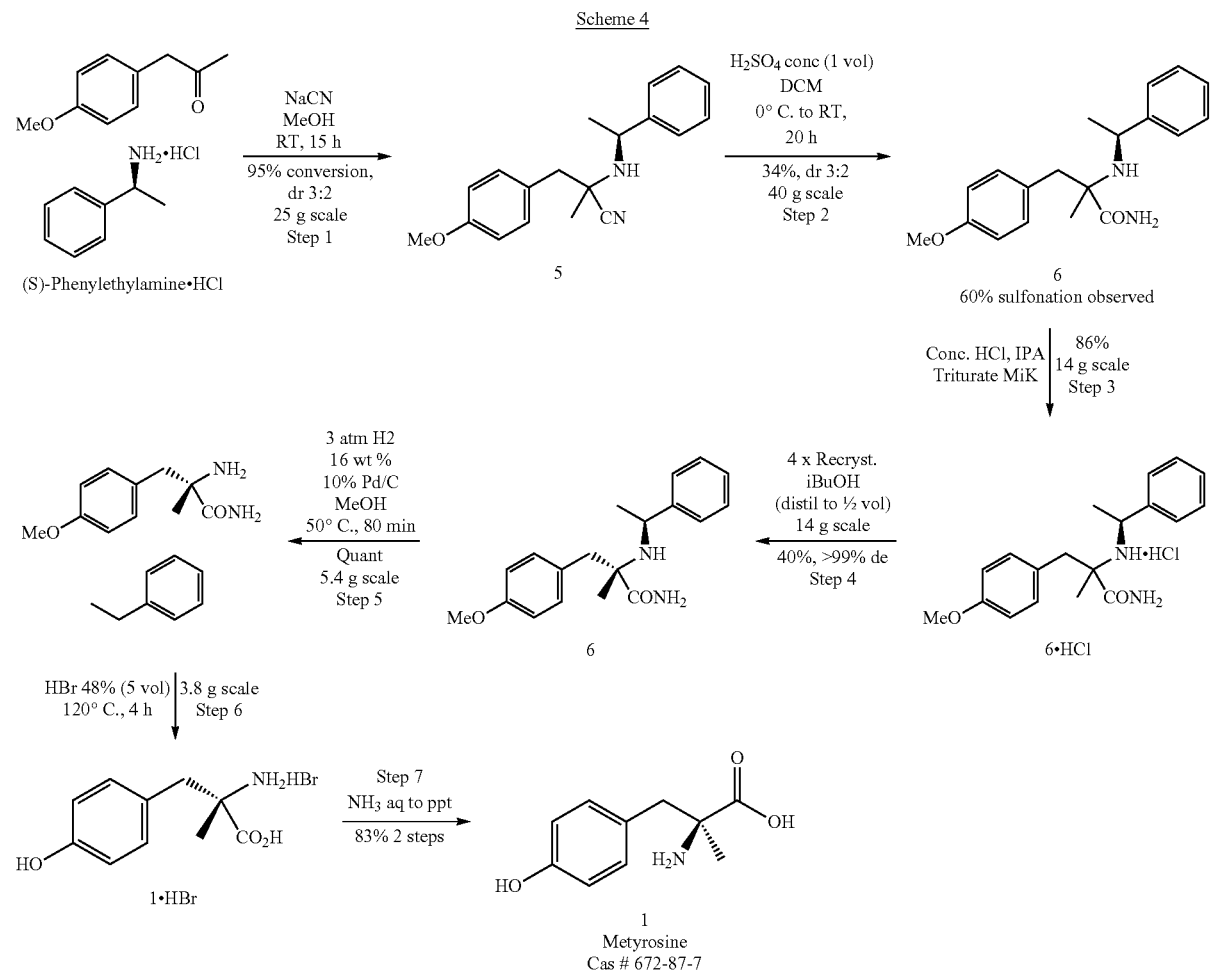

Example 7

(S)-Phenylethylamine hydrochloride

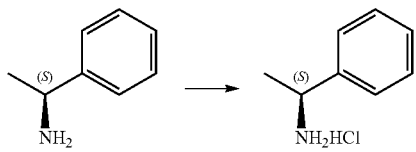

To a 500 mL flask were added (S)-phenylethylamine (BASF, ref: UN2735, 40.0 g, 333 mmol, 1 eq.) and MeOH (160 mL). The solution was cooled to 0° C. and 37% HCl (40 mL, 480 mmol, 1.44 eq.) were added dropwise. Concentration of the reaction mixture gave a white solid. Diethyl ether (300 mL) was added and the suspension was stirred for 15 min. The solid was filtered and was washed with diethyl ether (2×60 mL) to provide (S)-phenylethylamine hydrochloride (39.1 g, 75%) as a white solid. $^1$H NMR ($D_2O$, 400 MHz) 1.52 (d, J=7.2 Hz, 3H); 4.42 (q, J=7.2 Hz, 1H); 7.35-7.40 (m, 5H).

Example 8

3-(4-Methoxyphenyl)-2-methyl-2-(1-(S)-phenylethylamino)-propionitrile

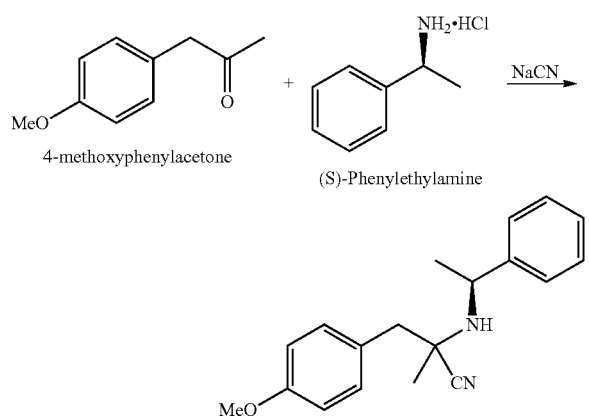

To a 500 mL flask were added (S)-phenylethylamine.HCl (25.0 g, 159.2 mmol, 1 eq.), MeOH (125 mL), NaCN (7.80 g, 159.2 mmol, 1 eq.) and 4-methoxyphenylacetone (Aldrich, ref: 19917-6. 24.5 mL, 159.2 mmol, 1 eq.). The mixture was stirred for 14 h at room temperature. The mixture was filtered, the filter cake was washed with MeOH (30 mL) and the filtrates were concentrated to an oil which was dissolved in $CH_2Cl_2$ (370 mL) and washed with water (250 mL). The organic phase was dried ($MgSO_4$) and concentrated in vacuo to provide 3-(4-methoxyphenyl)-2-methyl-2-(1-(S)-phenylethylamino)-propionitrile (47.2 g, 100% as a 6/4 mixture of diastereoisomers (S,S)/(R,S)), containing 5% of 4-methoxyphenylacetone) as a yellow oil. $^1$NMR ($CDCl_3$, 400 MHz) 1.05 (s, 0.62×3H); 1.27 (d, J=6.4 Hz, 0.6×3H); 1.40-1.44 (m, 0.4×6H); 2.47 (d, J=13.6 Hz, 0.4×1H); 2.74 (d, J=13.6 Hz, 0.4×1H); 2.84 (d, J=14 Hz, 0.6×1H) 2.94 (d, J=14 Hz, 0.6× 1H); 3.78 (s, 0.4×3H); 3.82 (s, 0.6×3H); 4.02 (q, J=6.4 Hz, 0.6×1H); 4.16 (q, J=6.4 Hz, 0.4×1H); 6.80-7.40 (m, 9H).

Example 9

3-(4-Methoxyphenyl)-2-methyl-2-(1-(S)-phenylethylamino)-propionamide 6

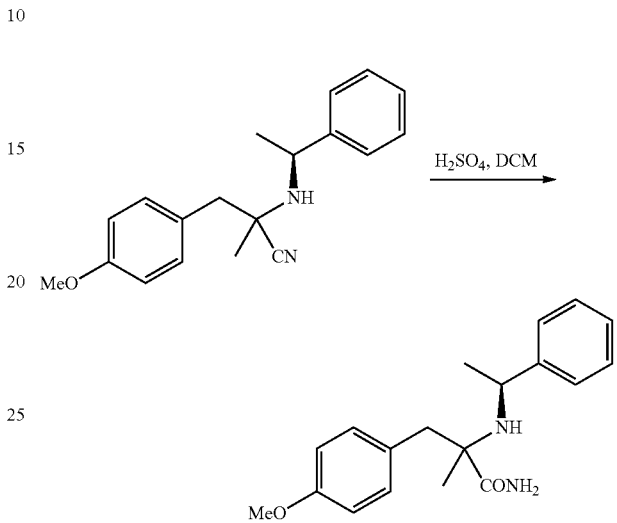

Method A.

To a 1 L flask with mechanical stirring under argon was added 3-(4-methoxyphenyl)-2-methyl-2-(1-(S)-phenylethylamino)-propionitrile 5 (40.0 g, 136.1 mmol) dissolved in $CH_2Cl_2$ (400 mL). The solution was cooled to −5° C. (using an ice salt bath) and conc. $H_2SO_4$ (40 mL) was added dropwise maintaining the temperature between −5° C. and 5° C. The mixture was warmed to RT over 2 h and was stirred for 16 h. Ice (400 g) was added and the mixture was stirred for 40 min. The two phases were separated and the aqueous phase was neutralized to pH 8-9 with 32% aq. $NH_3$. The aqueous phase was extracted with EtOAc (3×350 mL). The combined organic layers were dried ($MgSO_4$) and were concentrated in vacuo to provide 6 (14.2 g, 34%, 98% chemical purity by HPLC/MS) as a 6/4 mixture of diastereoisomers (S,S)/(R,S)) as a yellow oil.

Method B.

In a 250 mL flask was dissolved 3-(4-methoxyphenyl)-2-methyl-2-(1-(S)-phenylethylamino)-propionitrile 5 (5.0 g, 17.0 mmol) in $CH_2Cl_2$ (50 mL). The solution was cooled to 0° C. and conc. $H_2SO_4$ (2.5 mL) was added dropwise. The mixture was stirred at 40° C. for 28 h, was cooled to RT and ice (50 g) was added. The mixture was stirred for 1 h and the phases separated. The aqueous phase was basified to pH 8-9 using 32% aq. $NH_3$ and was extracted with EtOAc (3×50 mL). The combined organic layers were dried ($MgSO_4$) and concentrated in vacuo to provide 6 (3.32 g, 62%, 97% purity by HPLC/MS) as a 6/4 mixture of diastereoisomers (S,S)/(R,S)) as a yellow oil. $^1$H NMR ($CDCl_3$, 400 MHz) 1.13 (s, 0.4×3H); 1.15 (s, 03×3H) 1.24 (d, J=6.6 Hz, 0.4×3H); 1.30 (d, J=6.6 Hz 0.6×3H); 2.75 (d, J=13.4 Hz, 0.6×1H); 2.78 (d, J=13.6 Hz, 0.4×1H); 2.84 (d, J=13.4 Hz, 0.6×1H) 3.32 (d, J=13.6 Hz, 0.4×1H); 3.78 (s, 0.6×3H); 3.80 (s, 0.4×3H); 3.85 (q, J=6.6 Hz, 0.6×1H); 4.16 (q, J=6.6 Hz, 0.4×1H); 6.80-7.40 (m, 9H).

HPLC/MS $t_R$=4.21 min [(S,S)-6 MS (ESI (+)) m/z 313.2 (M+1)] and 4.34 min [(R,S)-6 MS (ESI (+)) m/z 313.2 (M+1)].

Example 10

3-(4-Methoxyphenyl)-2-(S)-methyl-2-(1-(S)-phenyl-ethylamino)-propionamide hydrochloride

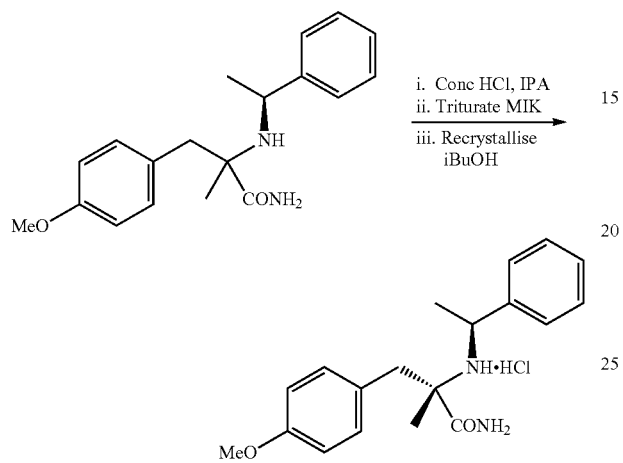

In a 500 mL flask was dissolved amide 6 (14.2 g, 45.5 mmol, 1 eq.) in i-PrOH (140 mL). Conc. HCl (5.7 mL, 68.3 mmol, 1.5 eq.) was added dropwise and the mixture was stirred for 20 min. The solvent was evaporated in vacuo and methyl isobutyl ketone (200 mL) was added. The mixture was heated to reflux temperature, was cooled to room temperature and was stirred for 72 h. The solids were collected by filtration, washed with methyl isobutyl ketone (20 mL) and dried in vacuo to provide 6.HCl (13.6 g, 86%, diasteremeric ratio (dr) 63/37(i.e., 63% diastereomeric purity of the S,S diastereomer)) as a white solid.

Example 11

Purification (Enhancing Diastereomeric Purity) of 6.HCl by Crystallization

In a 250 mL flask were placed amide hydrochloride 6.HCl (13.6 g, dr 37/63) and i-BuOH (136 mL). The mixture was heated to reflux temperature and i-BuOH (95 mL) was distilled. The mixture was cooled to room temperature and was stirred overnight. The solids were collected by filtration and were washed with i-BuOH to provide 6.HCl (11.6 g, 85%, dr 73/27 as a white solid.

This solid was dissolved in i-BuOH (139 mL) and was heated to reflux temperature. i-BuOH (70 mL) was distilled and the mixture was cooled to room temperature and was stirred for 3 h. Filtration provided 6.HCl (7.5 g, 65%, dr 88/12) as a white solid.

This solid was dissolved in i-BuOH (130 mL) and was heated to reflux temperature. i-BuOH (65 mL) was distilled and the mixture was cooled to room temperature and was stirred for 3 h. Filtration provided 6.HCl (6.0 g, 80%, dr 99/1) as a white solid.

This solid was dissolved in i-BuOH (105 mL) and was heated to reflux temperature. i-BuOH (53 mL) was distilled and the mixture was cooled to room temperature and was stirred for 16 h. Filtration provided 6.HCl (5.4 g, 90%, dr>99/1, 100% purity by HPLC/MS, 40% overall yield (67% theoretical yield)) as a white solid. $^1$H NMR (DMSO, 400 MHz) 1.06 (s, 3H); 1.57 (d, J=6.4 Hz, 3H); 2.84 (d, J=13.2 Hz, 1H); 3.27 (d, J=13.2 Hz, 1H); 3.69 (s, 3H) 4.40 (bs, 1H); 6.83 (d, J=8.4 Hz, 2H); 6.98 (d, J=8.4 Hz, 2H); 7.37-45 (m, 2H); 7.50-7.65 (m, 2H); 7.80 (bs, 1H); 9.40 (bs, 2H). HPLC/MS $t_R$=4.21 min [(S,S)-6.HCl MS (ESI (+)) m/z 313.2 (M+1)].

Example 12

2-(S)-Amino-3-(4-methoxyphenyl)-2-methyl-propionamide hydrochloride

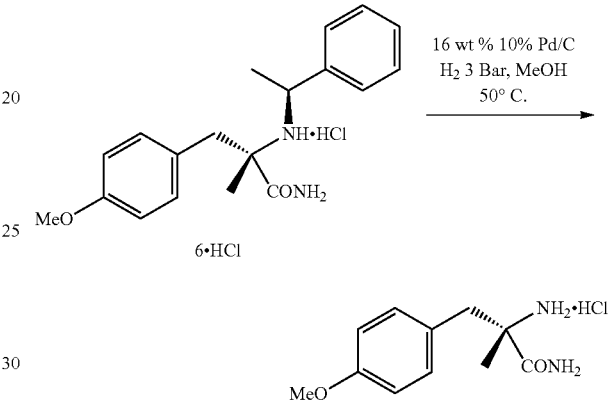

Amine 6.HCl (5.40 g, 15.5 mmol, 1 eq) was dissolved in MeOH (60 mL) and 10% Pd/C (2.0 g, 56% moisture content, 16% w/w) was added. The mixture was stirred under H$_2$ (3 bar) at 50° C. for 80 min. The mixture was filtered through celite and the filter pad was washed with MeOH (20 mL). The filtrates were concentrated in vacuo to provide 2-(S)-amino-3-(4-methoxyphenyl)-2-methyl-propionamide hydrochloride (3.80 g, 100%, 99.5% purity by HPLC/MS) as a yellow solid. $^1$H NMR (DMSO, 400 MHz) 1.46 (s, 3H); 3.02 (d, J=14 Hz, 1H); 3.10 (d, J=14 Hz, 1H), 3.72 (s, 3H); 6.87 (d, J=8.8 Hz, 2H); 7.15 (d, J=8.8 Hz, 2H); 7.64 (s, 1H); 7.94 (s, 1H); 8.08 (bs, 2H). HPLC/MS $t_R$=1.95 min. MS (ESI (+)) m/z=164.2 (M−CONH$_2$).

Example 13

Metyrosine 1

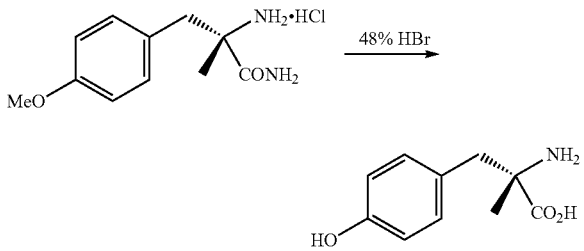

To a 100 mL flask with a reflux condenser were added 2-(5)-amino-3-(4-methoxyphenyl)-2-methyl-propionamide hydrochloride (3.80 g, 15.6 mmol) and 48% HBr (20 mL). The solution was heated for 4 h at 120° C., was cooled to room temperature and was concentrated in vacuo to give a beige paste. The paste was dissolved in water (15 ml) and the solution was again concentrated under vacuum. The paste was dissolved in H₂O (15 mL), the solution was heated to 65° C. and 300 mg of activated carbon were added. The mixture was stirred for 15 min, was filtered and the filter pad was washed with water (2×4 mL). The solution was heated to 55° C. and the pH was adjusted to 5-6 using 32% aq. NH₃. The mixture was cooled to 0° C. and was stirred for 15 min. Filtration, washing with cold water (2×5 mL) and drying in vacuo provided Metyrosine 1 (2.55 g, 83% yield, 99.6% HPLC purity, >99.5% ee) as a white solid. HPLC ((Zorbax C18, NaH₂PO₄ 10 mM pH=3/MeCN (100:0) 10 min, (100:0) to (0:100) 15 min, 0:100 5 min), $t_R$=10.1 min. Chiral HPLC (Nucleosil Chiral-1, CuSO₄ 10 mM/MeCN 10:1), $t_R$=16.9 min. m.p.=321-322° C. $[\alpha]_{546}$=+187° (c=0.5, Copper complex solution) Copper complex solution preparation: Solution A (anhydrous NaOAc dissolved in H₂O (150 mL) in 250 mL volumetric flask, glacial acetic acid (50 mL) added and diluted to volume with H₂O) mixed with Solution B (cupric sulfate (62.5 g) diluted to volume with H₂O in a 200 mL volumetric flask) in a 1 L volumetric flask and diluted to volume with H₂O. Sample prepared 5 mg/mL in this solution.

In order to obtain an NMR spectrum and taking into account the low solubility of the product, a small sample (10 mg) was transformed into its HCl salt. The sample was dissolved in 2 M HCl and the solution was evaporated to dryness. ¹H NMR (D₂O, 400 MHz) 1.49 (s, 3H); 2.90 (d, J=14.5 Hz, 1H); 3.16 (d, J=14.5 Hz, 1H); 6.75 (d, J=8.2 Hz, 2H), 7.01 (d, J=8.2 Hz, 2H).

Preparation of Metyrosine using L-alanine tert-butyl ester

Example 14

Synthesis of Aldimine

4-Chlorobenzaldehyde (3.87 g, 27.5 mmol) was dissolved in methanol (50 mL) and treated with triethylamine (3.87 g, 38.3 mmol, 1.39 equiv). The mixture was stirred for 7 min at ambient temperature followed by addition of L-alanine tert-butyl ester hydrochloride (5.00 g, 27.5 mmol). Magnesium sulfate (6.63 g, 55.1 mmol, 2 equiv) was added to this solution and the slurry was stirred for 17 h at ambient temperature. The solid was filtered and washed with methanol (6 mL). The filtrate was evaporated to dryness to result in an oily solid. This solid was dissolved in a biphasic MTBE/water (70 mL/20 mL) mixture. The organic phase was separated and washed with water (20 mL). The organic phase was dried over MgSO₄, the solid was filtered, and the filtrate was evaporated to dryness to afford aldimine 7 [7.09 g; 96.2%] as a clear oil, which became a solid when stored in a refrigerator. ¹H NMR (500 MHz, CDCl₃): δ 8.25 (br. s, 1H, ArCH), 7.71 (d, J=8.5 Hz, 2H, Ar), 7.38 (d, J=8.5 Hz, 2H, Ar), 4.04 (dq, J₁=0.6 Hz, J₂=6.8 Hz, 1H, CH), 1.48 (d, J=6.8 Hz, 3H, CH₃), 1.47 (s, 9H, 3×CH₃).

Example 15

Synthesis of tert-Butyl 2-Amino-3-(4-methoxyphenyl)-2-methylpropanoate

Aldimine (2.00 g, 7.47 mmol) and O-allyl-N-benzylcinchonidinium bromide (0.38 g, 0.75 mmol, 0.10 equiv) were mixed with toluene (20 mL) at ambient temperature. The mixture was stirred for 30 min and then was cooled to 0° C. Powdered KOH (2.10 g, 37.35 mmol, 5 equiv) was added at once to convert the thin slurry into a yellow solution. The mixture was stirred for 5 min and 4-methoxybenzyl bromide

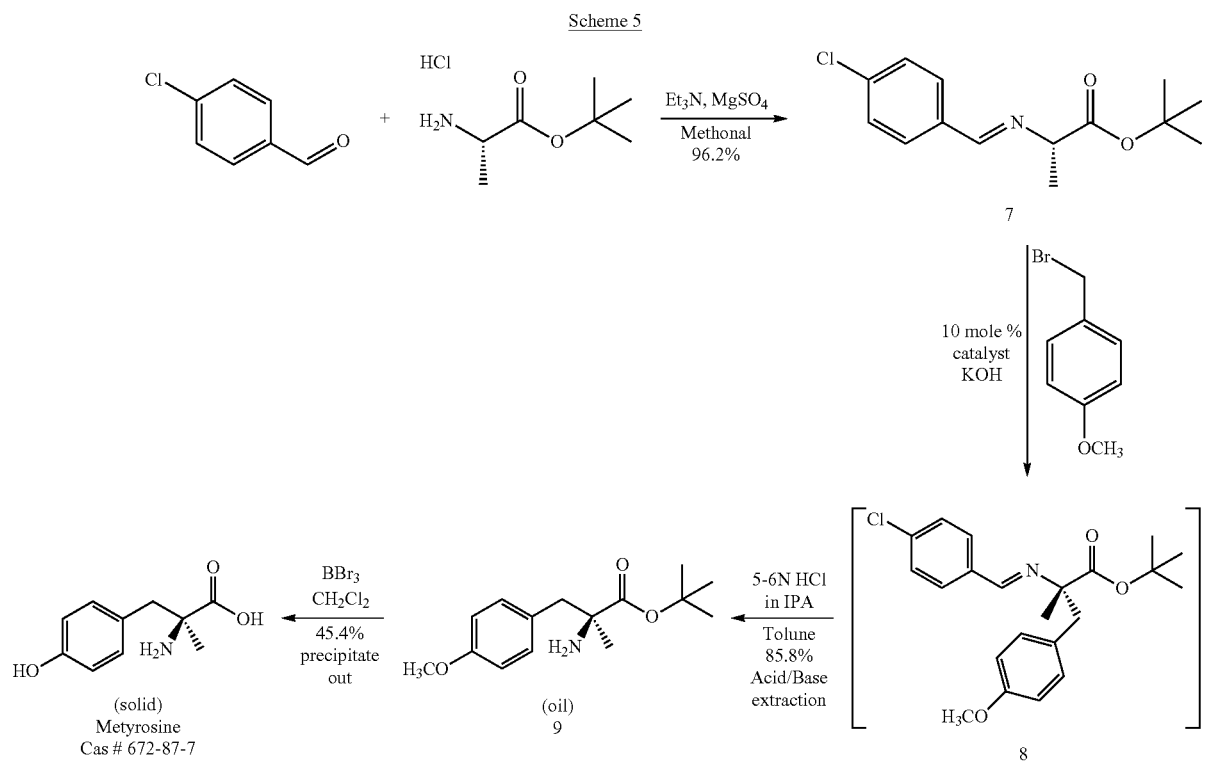

(7.51 g, 37.35 mmol, 5 equiv) was added at 0 to 1° C. The solution was allowed to warm and was stirred at ambient temperature for 16 h. The reaction mixture was sequentially washed with water (20 mL) and brine (20 mL), separated, and treated with a 5-6 N HCl solution in IPA (7 mL) for 1 h at ambient temperature. The reaction mixture was washed with water (20 mL). The aqueous phase was separated and treated with toluene (20 mL). The aqueous phase was separated, treated with a 2 N NaOH solution until basic, and the product was extracted with toluene (20 mL). The toluene phase was washed with brine (20 mL), separated, and dried over $Na_2SO_4$. The solid was filtered and the solvent was stripped to dryness to afford tert-butyl 2-amino-3-(4-methoxyphenyl)-2-methylpropanoate; 1.70 g; 85.8% as a clear oil. $^1$H NMR (500 MHz, $CDCl_3$): δ 7.13 (d, J=8.7 Hz, 2H, Ar), 6.81 (d, J=8.7 Hz, 2H, Ar), 3.78 (s, 3H, $CH_3$), 3.05 (d, J=13.3 Hz, 1H, $CH_2$), 2.71 (d, J=13.3 Hz, 1H, $CH_2$), 1.62 (br. s, 2H, $NH_2$), 1.45 (s, 9H, 3×$CH_3$), 1.32 (s, 3H, $CH_3$). $^1$H NMR analysis, carried out in the presence of 1.2 equiv of BINOL, resulted in 47.6% ee. Optical rotation ($\alpha^{25}{}_D$, chloroform, c=1.38): −9.06°.

Example 16

Synthesis of
2-Amino-3-(4-methoxyphenyl)-2-methylpropanoic
Acid Hydrochloride

Intermediate tert-butyl 2-amino-3-(4-methoxyphenyl)-2-methylpropanoate (0.60 g, 2.26 mmol) was mixed with toluene (6 mL) and a 5-6 N HCl solution in IPA (2 mL). A clear yellow solution was heated to reflux and kept at that temperature for 7 h. The resulting slurry was cooled to ambient temperature and filtered. The solid was washed with toluene (3 mL) on a filter and air-dried to afford 2-amino-3-(4-methoxyphenyl)-2-methylpropanoic acid hydrochloride [0.37 g; 67%] as a white solid [HPLC 71.8% (AUC; $t_R$=3.71]. $^1$H NMR (500 MHz, DMSO-$d_6$): δ 13.96 (br. s, 1H, COOH), 8.44 (br. s, 3H, $NH_3$), 7.16 (d, J=8.7 Hz, 2H, Ar), 6.90 (d, J=8.7 Hz, 2H, Ar), 3.74 (s, 3H, $CH_3$), 3.08 (s, 2H, $CH_2$), 1.48 (s, 3H, $CH_3$). Optical rotation ($\alpha^{25}{}_D$, DMSO, c=1.10)+7.27°.

Example 17

Synthesis of Metyrosine 1 tert-Butyl 2-amino-3-(4-methoxyphenyl)-2-methylpropanoate (0.30 g, 1.13 mmol) was dissolved in $CH_2Cl_2$ (3 mL) and $BBr_3$ (0.85 g, 3.39 mmol, 3 equiv) was added at room temperature. The reaction mixture was stirred for 1.5 h and treated with a $NaHCO_3$ solution to a basic pH. The aqueous phase was isolated. Solid started to precipitate in the aqueous phase in 30 min. Solid was filtered in 16 h and was washed on a filter with $CH_2Cl_2$ (2 mL) and water (2 mL). The solid was air-dried to afford metyrosine [0.10 g; 45.4%] as a white solid [HPLC 80.7% (Metyrosine; AUC; $t_R$=2.32 & 2.57]. $^1$H NMR (500 MHz, TFA-d): δ 8.60 (d, J=8.7 Hz, 2H, Ar), 8.39 (d, J=8.7 Hz, 2H, Ar), 4.91 (d, J=15.0 Hz, 1H, $CH_2$), 4.67 (d, J=15.0 Hz, 1H, $CH_2$), 3.30 (s, 3H, $CH_3$). Optical rotation ($\alpha^{30}{}_D$, c=1.080, l=10 mm, NaOAc/$CuSO_4$/$H_2O$/AcOH)+ 148.1.

Larger scale (e.g. >100 g) Synthesis Metyrosine using (R)-phenylglycinamide (Examples 18-24). Scheme 6 provides the general synthetic outline.

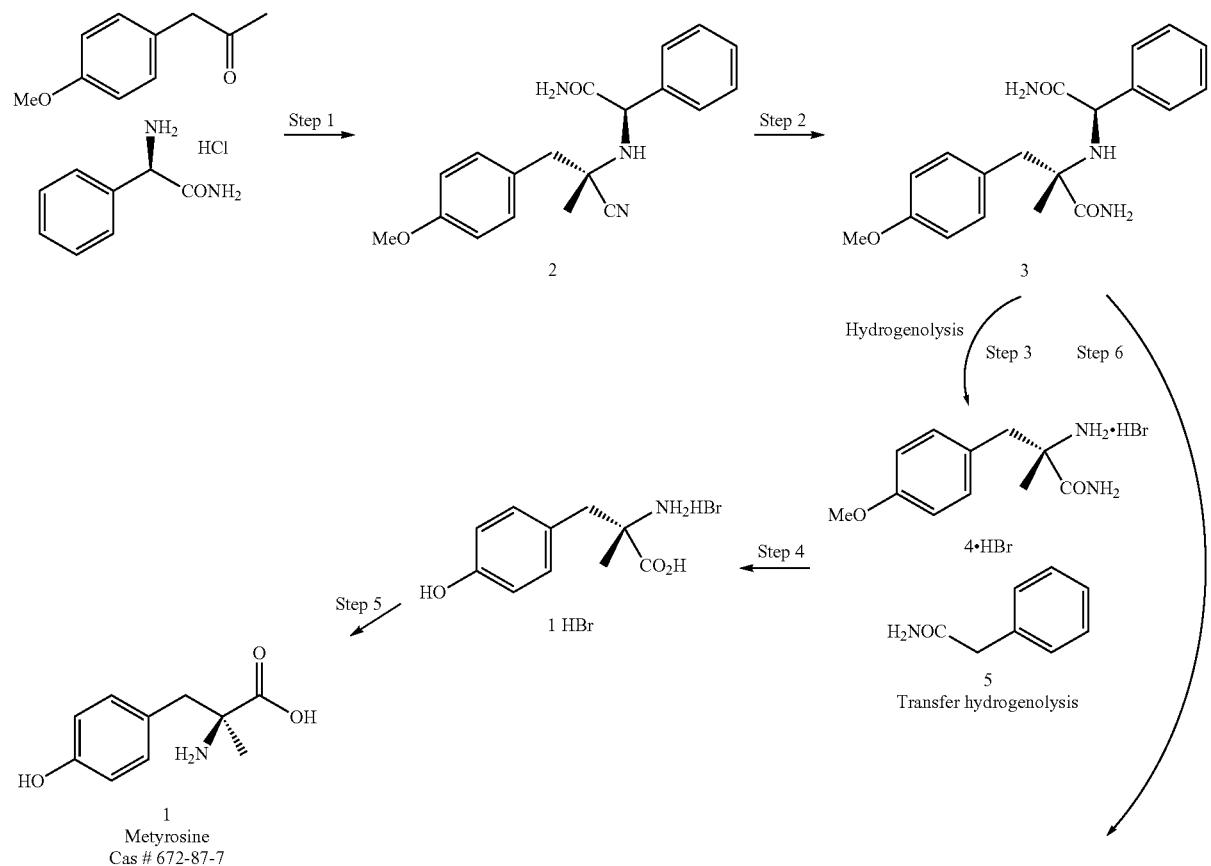

Scheme 6

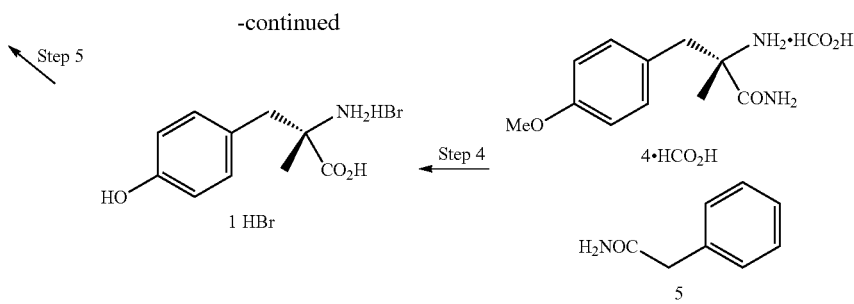

1) NaCN, MeOH/H₂O, 24 h, 44° C.; 2) H₂SO₄ conc, DCM, 15° C. to RT, 1.25 h: 3) a. 3 atm H₂, 6 wt % 10% Pd/C, MeOH, 55° C., 16 h, b. HBr aq; 4) HBr 48%, 105° C., 17 h; 5) NaOH aq; 6) 5 wt % 10% Pd/C, HCO₂H/H₂O MeOH, 55° C., 6 h

Example 18

2-[1-(S)-Cyano-2-(4-methoxyphenyl)-1-methylethylamino]-2-(R)-phenylacetamide 2

In a 5 L reactor equipped with anchor stirrer were charged (R)-phenylglycinamide.HCl (330 g, 1.77 mol, 1 eq.), MeOH (1.1 L), H₂O (1.9 L) and p-methoxyphenylacetone (290 g, 1.77 mol, 1 eq.). A solution of NaCN (86.7 g, 1.77 mol, 1 eq.) in H₂O (300 mL) was added over 15 min at room temperature. The mixture was stirred for 24 hours at 44° C. resulting in the formation of a yellow precipitate. The mixture was cooled to room temperature. The precipitate was filtered, was washed with H₂O/MeOH (7:3 v/v, 2×750 mL) and i-PrOH (2×500 mL). The solid was dried in vacuo (3 days) at 35° C. to provide 2-[1-(S)-Cyano-2-(4-methoxyphenyl)-1-methylethylamino]-2-(R)-phenylacetamide 2 (460 g, 80%, dr 97/3) as a yellow solid. ¹H NMR (400 MHz, CDCl₃) 1.14 (s, 3H), 2.90 (d, J=13.6 Hz, 1H), 2.99 (d, J=13.6 Hz, 1H), 3.20 (bs, 1H), 3.80 (s, 3H), 4.51 (s, 1H), 5.45 (bs, 1H), 5.75 (bs, 1H), 6.90 (d, J=8.6 Hz, 2H), 7.27 (d, J=8.6 Hz, 2H), 7.30-7.50 (m, 5H). ¹H NMR (R,R and S,S)-diastereoisomers of 2 (400 MHz, CDCl₃) 1.49 (s, 3H), 2.82 (d, J=13.8 Hz, 1H), 2.85 (d, J=13.8 Hz, 1H), 3.78 (s, 3H), 4.52 (s, 1H), 5.55 (bs, 1H), 6.60 (bs, 1H), 6.84 (d, J=8.6 Hz, 2H), 7.17 (d, J=8.6 Hz, 2H), 7.30-7.40 (m, 5H). dr determination: ¹H NMR comparing integration of peaks of 2 at 2.90/2.99 (1.00H, formally 2H) with those of its (R,R/S,S)-diastereoisomeric pair (prepared from nearly rac-phenylglycinamide) at 2.82/2.85 (0.03H, formally 2H).

Example 19

2-[(R)-(Carbamoylphenylmethyl)-amino]-3-(4-methoxyphenyl)-2-(S)-methylpropionamide 3

Into a 10 L reactor equipped with anchor stirrer was charged CH₂Cl₂ (1.64 L). The solvent was cooled to 15° C., then 95% H₂SO₄ (492 mL) and 2-[1-(S)-cyano-2-(4-methoxyphenyl)-1-methylethylamino]-2-(R)-phenylacetamide 2 (410 g, 1.27 mol) were added alternately in 9 portions over approximately 45 min (specifically: 164 mL of H₂SO₄ then 82 g of 2; subsequently, at approximately 5 min intervals, 8×[41 mL of H₂SO₄ then immediately 41 g of 2]). On addition of each portion, the suspension of 2 in the dense oily phase slowly dissolved (1-2 min) to provide a biphasic mixture. The resulting biphasic mixture (a red-brown dense oil with a pale yellow supernatant CH₂Cl₂ layer) was stirred for 0.5 h at 25° C. Ice-cold water (4.1 L) was added over 30 min, very slowly initially (200 mL dropwise over 15 min) due to a violent exotherm, and the biphasic mixture was stirred for 0.5 h. The phases were separated and the organic phase discarded. The combined aqueous phases were washed with CH₂Cl₂ (450 mL), and residual CH₂Cl₂ was stripped from the aqueous phase by distillation under vacuum at 55° C. (20-30 mBar). The aqueous solution was then cooled to 20° C. and was basified with 32% aq NH₃ (1150 mL) to pH 8-9 at such a rate that the temperature was kept below 28° C. (approximately 120 min). The suspension was stirred for 30 min to ascertain a stable pH. The white solid which formed was separated by filtration, washed with H₂O (2×2050 mL), and was thoroughly drained of water (but was not dried) to provide 2-[(R)-(carbamoylphenylmethy)-amino]-3-(4-methoxyphenyl)-2-(S)-methylpropionamide 3 (1087 g (391 g theoretical, the sample contains 64% w/w of H₂O), yield 90%, 97% HPLC purity, 96% de) as a wet white solid. HPLC (Luna C18, H₂O/MeCN 95:5 to 0:100 30 min, 254 nm, sample 2 mg/mL in MeOH). $t_R$(3)=15.3 min, 96% de. (2 degrades under these conditions: 3 peaks are detected at 17.7, 18.9 and 19.9 min). HPLC (R,R/S,S)-diastereoisomer of 3, $t_R$=15.0 min. de determination: HPLC comparing integration of peaks at $t_R$=15.3 min (97.3 area % 3) and $t_R$=15.0 min (1.6 area % (R,R)-diastereoisomer of 3 (reference (R,R/S,S) prepared from nearly rac-phenylglycinamide).

Example 20

Purification of 2-[(R)-(carbamoylphenylmethyl)-amino]-3-(4-methoxyphenyl)-2-(S)-methylpropionamide 3

2-[(R)-(Carbamoylphenylmethyl)-amino]-3-(4-methoxyphenyl)-2-(S)-methylpropionamide 3 (321 g, 941 mmol) and methyl isobutyl ketone (4173 mL) were heated to 72° C. until the solid was dissolved and the biphasic mixture (the minor lower aqueous layer is only visible on stopping stirring) was allowed to cool to room temperature with constant stirring. Stirring was maintained for 2 h. The solid formed was filtered at room temperature, was washed with methyl isobutyl ketone (2×320 mL) and was dried in vacuo to provide 2-[(R)-(carbamoylphenylmethyl)-amino]-3-(4-methoxyphenyl)-2-(S)-methylpropionamide 3 (268 g, 84%, >99.5% purity by HPLC) as a white solid. ¹H NMR (400 MHz, DMSO-d6) 1.04 (s, 3H), 2.35 (bs, 1H), 2.79 (d, J=12.8 Hz, 1H), 2.95 (d, J=12.8 Hz, 1H), 3.65 (s, 3H), 4.22 (s, 1H), 6.65 (d, J=8.4 Hz, 2H), 6.96 (d, J=8.4 Hz, 2H), 7.02 (bs, 1H), 7.05 (bs, 1H), 7.33-7.30 (m, 3H), 7.48 (d, J=7.2 Hz, 2H), 7.52 (bs, 1H), 7.64 (bs, 1H). HPLC (Luna C18, H₂O/MeCN 95:5 to 0:100 30 min, 254 nm, sample 2 mg/mL in MeOH) $t_R$=15.3 min, >99.5% purity. Mp: 106-108° C.

Example 21

Hydrogenolysis to provide 2-(S)-Amino-3-(4-methoxyphenyl)-2-methyl-propionamide hydrogen bromide salt 4.HBr To a 1 L hydrogenation reactor were added 2-[(R)-(carbamoylphenylmethy)-amino]-3-(4-methoxyphenyl)-2-(S)-methylpropionamide 3 (183.0 g, 537 mmol, 1 eq), MeOH (549 mL) and 10% Pd/C (19.4 g, 5 wt %). The mixture was stirred under $H_2$ (3 bar) at 51° C. for 8 h. Further 10% Pd/C (3.88 g, 1 wt %) was added and the mixture was stirred for a further 8 h at 53° C. The mixture was cooled to room temperature, was filtered through Celite and the filter pad was washed with MeOH (2×50 mL). The combined filtrates were concentrated at 30° C. under reduced pressure (rotary evaporator) to a dense white "stirrable" paste (250 mL) containing 2-(5)-amino-3-(4-methoxyphenyl)-2-methyl-propionamide 4 and 5.

$H_2O$ (75 mL) and 48% HBr (75 mL, 667 mmol, 1.25 eq.) were then added resulting in a white suspension. Residual MeOH was stripped from the mixture (45 mL distilled) by distillation at 100° C. (bath temperature) at reduced pressure (20-30 mBar). The resulting aqueous solution was cooled to room temperature and filtered; the solid was washed with $H_2O$ (50 mL). The white solid was discarded (containing phenylacetamide 5 and 4% 4.HBr by NMR) and the resulting solution of 4.HBr (approximately 400 mL, containing 23% 5 with respect to 4 by NMR) was used directly. $^1$H NMR (400 MHz, DMSO-6d) 4 1.14 (s, 3H), 2.10 (bs, 2H), 2.50 (d, J=13.1 Hz, 1H), 2.95 (d, J=13.1 Hz, 1H), 3.69 (s, 3H), 6.80 (d, J=8.5 Hz, 2H), 6.81 (bs, 1H), 6.90 (bs, 1H), 7.09 (d, J=8.5 Hz, 2H). Phenylacetamide 5 3.34 (s, 2H), 7.15-7.28 (m, 6H), 7.42 (bs, 1H). HPLC (Kromasil C8, $H_2O$/0.1% TFA/MeCN/ 0.07% TFA 95:5 to 0:100 30 min, 254 nm, 1 mg/mL in MeOH) phenylacetamide 5 $t_R$=11.21 min. 4 $t_R$=9.10 min. (3 $t_R$=11.95 min.).

Example 22

(−)-α-Methyl-L-tyrosine, Metyrosine 1

To a 2 L flask equipped with an anchor stirrer was charged the 4.HBr solution (519 mmol obtained from hydrogenolysis) and 48% HBr (648 mL) was added. The solution was heated for 17 h at 105° C. and was cooled to room temperature. The solution was washed with $CH_2Cl_2$ (8×80 mL, to remove traces of phenylacetic acid) and the aqueous phase was stripped of residual $CH_2Cl_2$ by distillation at 65° C. at reduced pressure (20-30 mBar). Activated carbon (10.5 g) was added and the mixture was stirred for 30 min at 60° C., was filtered at 60° C. and the filter pad was washed with water (2×35 mL) at RT. The combined filtrates were cooled to room temperature and were basified with 12.5 M NaOH (430 mL) to pH 6-7 at such a rate as to maintain the temperature below 30° C. (over approximately 2 h). The white solid formed was separated by filtration, was washed with $H_2O$ (2×315 mL) and was dried in vacuo to provide (−)-α-methyl-L-tyrosine, metyrosine 1 (87 g, 86%, >99.9% HPLC purity, no impurities detected, >99.9% ee the other enantiomer is not detected) as a white solid. HPLC (Zorbax C18, $NaH_2PO_4$ 10 mM pH=3/ MeCN (100:0) 10 min, (100:0) to (0:100) 15 min, 0:100 5 min, 225 nm, sample 1 mg/mL in 0.1 M HCl) $t_R$ (1)=7.6 min, $t_R$ (4)=13.95 min. Chiral HPLC (Nucleosil Chiral-1, $CuSO_4$ 10 mM/MeCN 9:1, 254 nm, sample 1 mg/mL in eluant) $t_R$=14.4 min. $t_R$ enantiomer=8.4 min. Mp: 309-313° C.

In order to obtain an NMR spectrum (taking into account the low solubility of the product), a small sample (10 mg) was transformed into its HCl salt. The sample was dissolved in 2 M HCl and the solution was evaporated to dryness. $^1$H NMR (400 MHz, $D_2O$) 1.49 (s, 3H), 2.90 (d, J=14.5 Hz, 1H), 3.16 (d, J=14.5 Hz, 1H), 6.75 (d, J=8.2 Hz, 2H), 7.01 (d, J=8.2 Hz, 2H).

Example 23

Transfer hydrogenolysis to provide 2-(S)-Amino-3-(4-methoxyphenyl)-2-methylpropionamide formic acid salt 4.HCOOH In a 5 L reactor equipped with anchor stirrer and oil bubbler, 2-[(R)-(carbamoylphenylmethyl)-amino]-3-(4-methoxyphenyl)-2-(S)-methylpropionamide 3 (261.8 g, 766.8 mmol) was dissolved in MeOH (1570 mL). A first batch of 10% Pd/C (22.2 g, 4% w/w) was added and the mixture was heated to 56° C. HCOOH (217 mL, 5.75 mol) was dissolved in $H_2O$ (393 mL) and 480 mL of the resulting solution were added to the mixture dropwise over 4.5 h, and the temperature was maintained between 54 and 60° C. When gas development ceased (as determined from the oil bubbler, approximately 30 min after complete addition of $HCO_2H$ aq), the mixture was cooled to room temperature and a second batch of 10% Pd/C (5.6 g, 1% w/w) was added. The mixture was heated again to 55° C. and the remaining HCOOH solution (130 mL) was added dropwise over 45 min. Stirring was maintained for a further 30 min. The mixture was cooled to room temperature, was filtered over a pad of Celite and the filter pad was washed with MeOH (2×100 mL). The combined filtrates were concentrated under reduced pressure (rotary evaporator) to a white "stirrable" paste (approximate volume 300 mL) containing 4.HCOOH and phenylacetamide 5.

$H_2O$ (100 mL) was added and residual MeOH was stripped by distillation at reduced pressure (20-30 mBar) at 70° C. The resulting solution (approximately 360 mL) was filtered and was washed with 100 mL of $H_2O$. The white solid (5 containing 1% of 4.HCOOH by NMR) was discarded and the resulting solution of 4.HCOOH (containing 13% of 5 with respect to 4 by NMR) was used directly. $^1$H NMR (400 MHz, DMSO-d6) 1.43 (s, 3H), 2.93 (d, J=13.6 Hz, 1H), 3.08 (d, J=13.6 Hz, 1H), 3.73 (s, 3H), 6.88 (d, J=8.8 Hz, 2H), 7.17 (d, J=8.8 Hz, 2H), 7.56 (s, 1H), 7.83 (s, 1H). Phenylacetamide 5 (200 MHz, DMSO-d6) 3.36 (s, 2H), 6.87 (bs, 1H), 7.20-7.33 (m, 5H), 7.45 (bs, 1H). HPLC (Kromasil C8, $H_2O$/0.1% TFA/MeCN/ 0.07% TFA 95:5 to 0:100 30 min, 254 nm, 1 mg/mL in MeOH) Phenylacetamide 5 $t_R$=11.38 min. 4.$HCO_2H$ $t_R$=9.11 min. (3 $t_R$=11.95 min).

Example 24

(−)-α-Methyl-L-tyrosine, Metyrosine 1

Into a 2 L reactor equipped with anchor stirrer, a solution of 4.HCOOH (760 mmol from transfer hydrogenolysis) and $H_2O$ (200 mL) was mixed with 48% aqueous HBr (948 mL, 8.43 mol). The resulting solution was heated to 105° C. for 17 h. The mixture was cooled to room temperature and was washed with $CH_2Cl_2$ (6×125 mL, to remove traces of phenylacetic acid), the aqueous phase was stripped of residual $CH_2Cl_2$ at 60° C. at reduced pressure (20-30 mBar). The solution was mixed with activated carbon (15.6 g, 10% w/w) and was heated to 60° C. for 30 min. The mixture was filtered at 60° C. and the residue was rinsed with $H_2O$ (2×60 mL). The combined filtrates were cooled to 15° C. and were basified with 12.5 M NaOH (730 mL) to pH 6-7 at such a rate as to maintain the temperature below 30° C. (over approximately 100 min). The white solid formed was separated by filtration, was washed with H$_2$O (2×460 mL) and IPA (490 mL and 245 mL) and was dried to provide (−)-α-methyl-L-tyrosine, Metyrosine 1 (121.1 g, 82%, >99.9% HPLC no impurities >0.1% detected; >99.9% ee., the other enantiomer is not detected) as a white solid. HPLC (Zorbax C18, NaH$_2$PO$_4$ 10 mM pH=3/MeCN (100:0) 10 min, (100:0) to (0:100) 15 min, 0:100 5 min, 225 nm, sample 1 mg/mL in 0.1 M HCl) $t_R$ (1)=7.6 min; $t_R$ (4)=13.95 min. Chiral HPLC (Nucleosil Chiral-1, CuSO$_4$ 10 mM/MeCN 9:1, 254 nm, sample 1 mg/mL in eluant) $t_R$=14.3 min. $t_R$ enantiomer=8.4 min. Mp: 308-313° C.

While certain embodiments have been illustrated and described, it should be understood that changes and modifications can be made therein in accordance with ordinary skill in the art without departing from the technology in its broader aspects as defined in the following claims.

The embodiments, illustratively described herein may suitably be practiced in the absence of any element or elements, limitation or limitations, not specifically disclosed herein. Thus, for example, the terms 'comprising,' 'including,' 'containing,' etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and compounds within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, or compounds, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' 'at least,' 'greater than,' 'less than,' and the like, include the number recited and refer to ranges which can be subsequently broken down into subranges as discussed above. Finally, as will be understood by one skilled in the art, a range includes each individual member.

Other embodiments are set forth in the following claims.

What is claimed is:

1. A process for the synthesis of Metyrosine, comprising contacting a compound of Formula I:

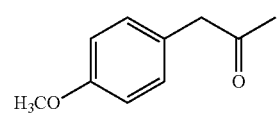

with a compound of Formula IA

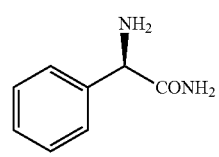

or an acid addition salt thereof,
to give a product comprising a compound of Formula II:

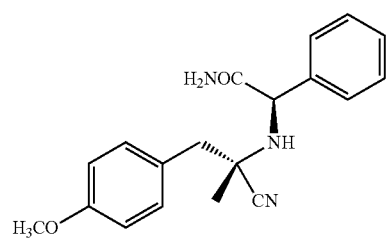

or an acid addition salt thereof,
wherein:
the contacting takes place in a methanol:water solution comprising about 1:2 methanol:water (vol:vol) in the presence of cyanide (CN);
the product comprising the compound of Formula II or acid addition salt thereof selectively precipitates from the methanol:water solution; and
the product comprising the compound of Formula II or acid addition salt thereof that precipitates from the methanol:water solution includes the compound of Formula II in about 80% yield and at least about 95% diastereomeric purity.

2. The process of claim 1 further comprising contacting the compound of Formula II or an acid addition salt thereof with a hydrolyzing agent selected from the group consisting of an acid, a base, a hydroperoxide, and an enzyme to provide a compound of Formula III

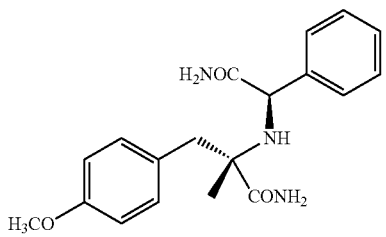

or an acid addition salt thereof.

3. The process of claim 2, wherein the hydrolyzing agent is a a Bronsted acid.

4. The process of claim 2, further comprising hydrogenolyzing the compound of Formula III or an acid addition salt thereof to provide a compound of Formula V:

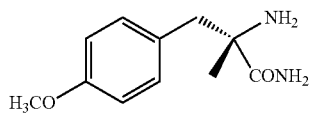

or an acid addition salt thereof.

5. The process of claim 4, further comprising contacting the compound of Formula V or an acid addition salt thereof with an acid to provide Metyrosine:

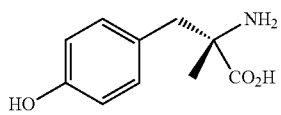

or an acid addition salt thereof.

6. A process for the synthesis of Metyrosine, comprising contacting a compound of Formula I:

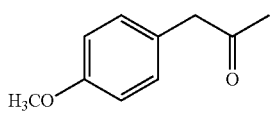

with a compound of Formula IA

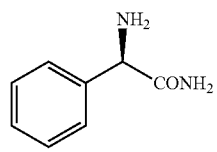

or an acid addition salt thereof, to give a product comprising a compound of Formula II:

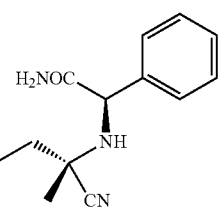

or an acid addition salt thereof, wherein:

the contacting takes place in a methanol:water solution comprising about 1:2 methanol:water (vol:vol) in the presence of cyanide ($CN^-$);

the product comprising the compound of Formula II or acid addition salt thereof selectively precipitates from the methanol:water solution; and the product comprising the compound of Formula II or acid addition salt thereof that precipitates from the methanol:water solution includes the compound of Formula II in at least about 95% diastereomeric purity.

7. The process of claim 6, wherein the product comprising the compound of Formula II or acid addition salt thereof that precipitates from the methanol:water solution includes the compound of Formula II in at least about 60% yield.

8. The process of claim 7, wherein the product comprising the compound of Formula II or acid addition salt thereof that precipitates from the methanol:water solution includes the compound of Formula II in at least about 75% yield.

* * * * *